US011229629B2

(12) United States Patent
Wu et al.

(10) Patent No.: US 11,229,629 B2
(45) Date of Patent: Jan. 25, 2022

(54) INHIBITORS OF MITOCHONDRIAL FISSION

(71) Applicant: Queen's University at Kingston, Kingston (CA)

(72) Inventors: Danchen Wu, Kingston (CA); Michael Wells, Kingston (CA); Stephen Archer, Kingston (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 16/831,944

(22) Filed: Mar. 27, 2020

(65) Prior Publication Data
US 2020/0323829 A1    Oct. 15, 2020

Related U.S. Application Data

(60) Provisional application No. 62/826,247, filed on Mar. 29, 2019.

(51) Int. Cl.
*A61K 31/437* (2006.01)
*A61P 35/00* (2006.01)
*A61K 31/404* (2006.01)

(52) U.S. Cl.
CPC .......... *A61K 31/437* (2013.01); *A61K 31/404* (2013.01); *A61P 35/00* (2018.01)

(58) Field of Classification Search
None
See application file for complete search history.

(56) References Cited

U.S. PATENT DOCUMENTS

2017/0312332 A1* 11/2017 Mochly-Rosen ...... A61K 38/08

OTHER PUBLICATIONS

Sieveking et al, Bioorganic & Medicinal Chemistry, 22, pp. 4609-4620 (Year: 2014).*
Nishiyama et al, European Journal of Medicinal Chemistry, vol. 136, pp. 1-13 (Year: 2017).*
Cassidy-Stone, A., et al., "Chemical Inhibition of the Mitochondrial Division Dynamin Reveals Its Role in Bax-Bak-Dependent Mitochondrial Outer Membrane Permeabilization", Dev. Cell, 14, pp. 193-204, (2008).
Archer, S.L., "Mitochondrial Dynamics—Mtiochondrial Fission and Fusion in Human Diseases", New England Journal of Medicine, 369;23, pp. 2236-2251, (2013).
Bordt, E.A., et al., "The Putative Drp1 inhibitor mdivi-1 is a Reversible Mitochondrial Complex 1 Inhibitor that Modulates Reactive Oxygen Species", Dev. Cell, 40, pp. 583-594, (2017).
Kitamura, S., et al., "Drp1 expression levels correlate with clinical stage in extramammary Paget's disease", European Academy of Dermatology and Venereology, 34, pp. e433-e531, (2020).
Moran, M.D., et al., "KRAS Mutation Status is Associated with Enhanced Dependency on Folate Metabolism Pathways in Non-Small Cell Lung Cancer Cells", Mol. Cancer Ther. 13(6), pp. 1611-1624, (2014).
Yu, L. el al., "The expression and prognostic significance of Drp1 in lung cancer", Medicine, 96:48, pp. 1-11, (2019).

* cited by examiner

*Primary Examiner* — Zinna Northington Davis
(74) *Attorney, Agent, or Firm* — Angela Lyon

(57) ABSTRACT

Pharmaceutical compositions that include inhibitors of mitochondrial fission are described for the treatment and/or mitigation of cancer, pulmonary arterial hypertension, cardioprotection, stroke, coronary heart disease, neurological disorder, a neurodegenerative disease, Parksinonism, Huntington's Chorea, Alzheimer's disease, diabetic cardiomyopathy, fatty liver diseases, non-alcoholic fatty liver diseases, or alcohol-related liver disease.

7 Claims, 8 Drawing Sheets

Specification includes a Sequence Listing.

SEQUENCE LISTING

<160> NUMBER OF SEQ ID NOS: 2

<210> SEQ ID NO 1
<211> LENGTH: 25
<212> TYPE: RNA
<213> ORGANISM: Homo sapiens

```
<400> SEQUENCE: 1
cccuagcugu aaucacuaaa cuuga                                 25

<210> SEQ ID NO 2
<211> LENGTH: 27
<212> TYPE: RNA
<213> ORGANISM: Homo sapiens

<400> SEQUENCE: 2
uugggaucga cauuagugau uugaacu                               27
```

INHIBITORS OF MITOCHONDRIAL FISSION

RELATED APPLICATION

This application claims the benefit of the filing date of U.S. Application No. 62/826,247, filed on Mar. 29, 2019, the contents of which are incorporated herein by reference in their entirety.

FIELD

The invention relates to inhibitors of mitochondrial fission and uses thereof.

BACKGROUND

Mitochondria exist in a dynamic network, continuously joining together (a process termed mitochondrial fusion) and separating (termed mitochondrial fission). Fission and fusion, along with mitochondrial motility, are noncanonical functions of these organelles which in aggregate are called mitochondrial dynamics. Mitochondrial dynamics is regulated by a variety of enzymes, most of which are large GTPase. (GTPase is a family of hydrolase enzymes that can bind and hydrolyze guanosine triphosphate (GTP)). Mitochondrial fission is primarily mediated by a large GTPase known as dynamin-related protein 1 (Drp1). When cytosolic Drp1 is activated, it translocates to outer mitochondrial membrane, polymerizes, and hydrolyzes GTP. On the outer mitochondrial membrane, activated Drp1 interacts with one or more of its four binding partners. These binding partners are mitochondrial dynamics protein of 49 kDa, mitochondrial dynamics protein of 51 kDa, mitochondrial fission 1 protein, and mitochondrial fission factor. These nuclear encoded proteins are anchored on the outer mitochondrial membrane where they facilitate mitochondrial fission. Drp1's GTPase activity is essential for outer mitochondrial membrane constriction. The current standard inhibitor of Drp1 is mitochondrial division inhibitor 1 (mdivi-1), which was identified by Cassidy-Stone et al. (Cassidy-Stone A, et al., *Dev Cell*. 2008; 14:193-204).

This standard inhibitor has been used to understand physiologic and pathologic functions of Drp1. Drp1 inhibition by mdivi-1 has been shown to reduce ischemia-reperfusion injury in the kidney and heart by inhibiting pathologic fission (Tian L, et al., *J Mol Med* (Berl), 2017; 95:381-393; Sharp W W, et al., *FASEB J*. 2014; 28:316-26; Sumida M, et al., *J Am Soc Nephrol*. 2015; 26:2378-87). In addition, mdivi-1 has been used to study diseases characterized by excessive cell proliferation and increased Drp1 expression and/or activity. Such diseases include cancer and pulmonary arterial hypertension. Mdivi-1 regresses cancer and pulmonary arterial hypertension in pre-clinical models. Mdivi-1 and small interfering RNA targeting Drp1 (siDrp1) have been shown to inhibit mitotic fission leading to cell cycle arrest and induce apoptosis (Archer S. L., *N. Engl. J. Med.* 2013; 369:2236-51). There are concerns about specificity of mdivi-1 (Bordt E. A., et al., *Dev Cell*. 2017; 40:583-594 e6). There is a need for potent and specific Drp1 GTPase inhibitors.

SUMMARY

In one aspect, the invention provides a pharmaceutical composition comprising a compound of Formula 1 or a pharmaceutically acceptable salt thereof, and a pharmaceutically acceptable vehicle:

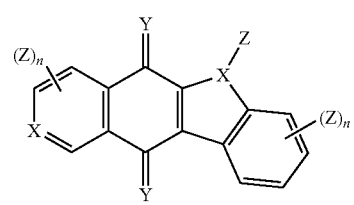

(1)

where X is N or C;

Y is O or S;

Z is a substituent that may be further substituted; and n is 1-4, wherein a substituent comprises alkyl, alkenyl, alkynyl, aryl, aryl-halide, heteroaryl, cyclyl, Si(alkyl)$_3$, Si(alkoxy)$_3$, halo, alkoxyl, amino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, or a combination thereof.

In various embodiments, the pharmaceutical composition is for the treatment and/or mitigation of one or more of cancer, pulmonary arterial hypertension, cardioprotection, stroke, coronary heart disease, neurodegenerative diseases, Parksinonism, Huntington's Chorea, Alzheimer's disease, diabetic cardiomyopathy, fatty liver diseases, non-alcoholic fatty liver diseases, and alcohol-related liver disease. In one embodiment, the pharmaceutically acceptable vehicle is an excipient. In one embodiment, the cancer is metastatic cancer. In one embodiment, the metastatic cancer is breast cancer, ovarian cancer, lung cancer, pancreatic cancer, melanoma, colorectal cancer, kidney cancer, cervical cancer, testicular cancer, or liver cancer. In one embodiment, the pharmaceutical composition further comprises one or more antineoplastic agent(s). In one embodiment, the compound of Formula 1 is

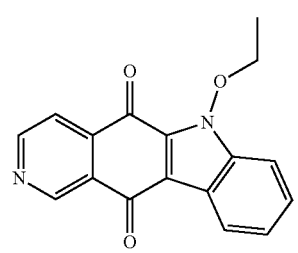

Compound 12 "Drpitor1"

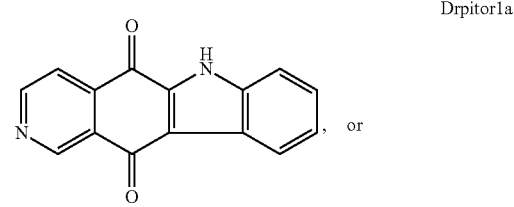

Drpitor1a

, or

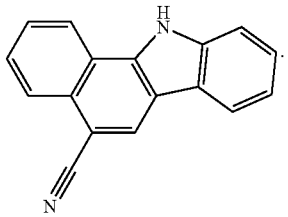

Compound 13

In one embodiment, the compound of Formula 1 is Drpitor1a. In one embodiment, the compound of claim 1 is present in an amount from 1 to 1000 mg.

In one aspect, the invention provides a method of reducing or inhibiting mitochondrial fission, comprising administering to a subject in need thereof a pharmaceutical composition comprising a compound of Formula (1). In one embodiment, the compound of Formula (1) is Compound 12 "Drpitor1", Drpitor1a, or compound 13. In one embodiment, the mitochondrial fission is associated with one or more of cancer, pulmonary arterial hypertension, cardioprotection, stroke, coronary heart disease, a neurodegenerative disease, Parksinonism, Huntington's Chorea, Alzheimer's disease, diabetic cardiomyopathy, fatty liver diseases, non-alcoholic fatty liver diseases, and alcohol-related liver disease. In one embodiment, the cancer is metastatic cancer. In one embodiment, the metastatic cancer is breast cancer, ovarian cancer, lung cancer, pancreatic cancer, melanoma, colorectal cancer, kidney cancer, cervical cancer, testicular cancer, or liver cancer. In one embodiment, the effective amount is an amount from 1 to 1000 mg. In one embodiment, the effective amount is an amount from 5 to 500 mg.

In one aspect, the invention provides use of a compound of Formula (1) for preparation of a medicament for treating and/or mitigating one or more of cancer, pulmonary arterial hypertension, cardioprotection, stroke, coronary heart disease, neurological disorder, Parkinson's disease, Alzheimer's disease, or Huntington's disease.

In various embodiments, the compound of Formula (1) is compound 12 "Drpitor1", Drpitor1a, or compound 13. In one embodiment, the cancer is metastatic cancer. In one embodiment, the metastatic cancer is breast cancer, ovarian cancer, lung cancer, pancreatic cancer, melanoma, colorectal cancer, kidney cancer, cervical cancer, testicular cancer, or liver cancer.

BRIEF DESCRIPTION OF THE DRAWINGS

For a better understanding of the invention and to show more clearly how it may be carried into effect, reference will now be made, by way of example, to the accompanying drawings, wherein:

FIG. 2 shows a synthetic route to Drpitor1 and Drpitor1a.

FIG. 8B is a graph of RVSP and RVEDP vs. time (−10 min is when treatment with Drpitor-1a (0.5 μM) in DMSO was added to the perfusate; 0 min is when a first ischemia was started) from IR experiments in hearts treated with Drpitor1a.

DESCRIPTION

Definitions

Figure 1:
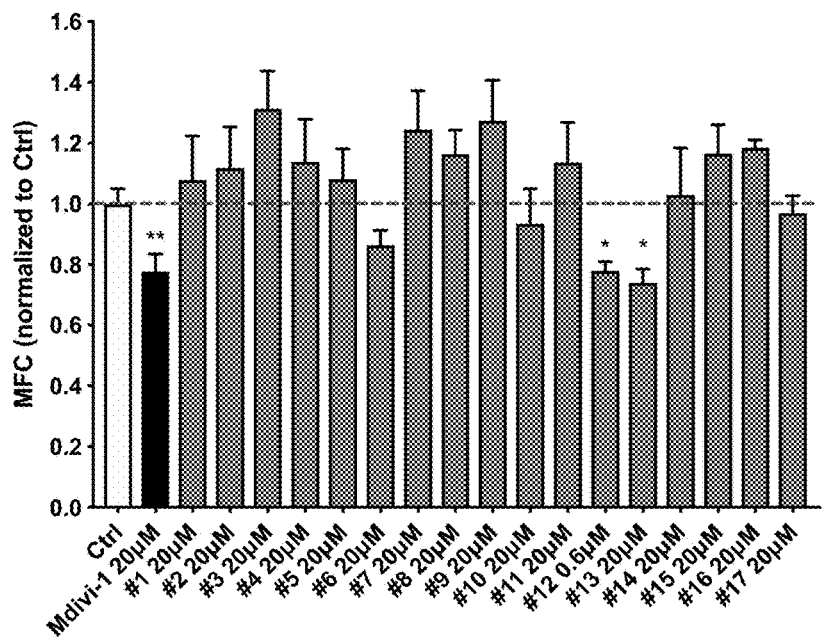
FIG. 1 is a bar graph depicting mitochondrial fragmentation count (MFC) of test compounds on A549 cells showing significant inhibition of mitochondrial fragmentation achieved by compound #12, which is referred to herein as Drpitor1, and compound #13 (see Table 1), treatment. n=5-10/group, *$P<0.05$ vs Ctrl, **$P<0.01$ vs Ctrl.

As used herein, the term "Annexin V" refers to a protein that is used to detect apoptotic cells.

As used herein, the term "BUN" refers to blood urea nitrogen.

As used herein, the term "Ctrl" refers to a control sample.

As used herein, the term "DMSO" refers to dimethylsulphoxide.

As used herein, the term "EdU" refers to 5-ethynyl-2'-deoxyuridine.

As used herein, the term "Dipitor1" refers to a compound as shown in Tables 1 and 3.

As used herein, the term "Dipitor1a" refers to a compound as shown in Table 3.

As used herein, the term "Drp1" refers to dynamin-related protein 1.

As used herein, the term "Dyngo4a" refers to a compound that is a positive control for dynamin-1 GTPase inhibitor (see Table 3)(McCluskey A, et al., *Traffic.* 2013; 14(12): 1272-89).

As used herein, the term "FCCP" refers to carbonyl cyanide-4-(trifluoromethoxy)phenylhydrazone.

As used herein, the term "GTPase" refers to a family of hydrolase enzymes that can bind and hydrolyze guanosine triphosphate (GTP).

As used herein, the term "IR" refers to ischemia-reperfusion.

As used herein, the term "MFC" refers to mitochondrial fragmentation count.

As used herein, the term "mdivi-1" refers to mitochondrial division inhibitor 1.

As used herein, the term "mDrp1 WT" refers to wild type mouse Drp1 plasmid.

As used herein, the term "mDrp1 K38A" refers to mutant mouse Drp1 plasmid in which lysine 38 is substituted by alanine.

As used herein, the term "MitoSOX" refers to a mitochondrial superoxide indicator.

As used herein, the term "PAH" refers to pulmonary arterial hypertension.

As used herein, the term "PASMC" refers to pulmonary artery smooth muscle cells.

As used herein, the term "ROS" refers to reactive oxygen species.

As used herein, the term "RV" refers to right ventricle.

As used herein, the term "RV-IR" refers to right ventricle ischemia-reperfusion.

As used herein, the term "RVSP" refers to right ventricular systolic pressure.

As used herein, the term "RVEDP" refers to right ventricular end-diastolic pressure.

As used herein, "substituted" means having one or more substituent moieties whose presence does not interfere with the desired reactivity. Examples of substituents include alkyl, alkenyl, alkynyl, aryl, aryl-halide, heteroaryl, cyclyl (non-aromatic ring), Si(alkyl)$_3$, Si(alkoxy)$_3$, halo, alkoxyl, amino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, or a combination thereof.

As used herein, the term "siDrp1" refers to small interfering RNA against Drp1.

As used herein, the term "TMRM" refers to tetramethylrhodamine methyl ester.

The term "effective amount" encompasses the term "dose" or "dosage," and is intended to refer to the quantity of pharmaceutically active ingredient administered to the individual in need thereof capable of producing the desired therapeutic effect. The term may refer to a single one time dose, in a physically discrete unit, such as, for example, in a pill or injection or may refer to multiple doses in physically discrete units. The term "effective amount" also encompasses the quantity of pharmaceutically active ingredient administered to the individual, expressed as the number of molecules, moles, grams, or volume per unit body mass of the individual, such as, for example, mol/kg, mg/kg, ng/kg, ml/kg, or the like, sometimes referred to as concentration administered. The effective amount of pharmaceutically active ingredient may vary among individuals and may fluctuate within an individual over time, depending on factors such as, but not limited to, the condition being treated, genetic profile, metabolic rate, biotransformation capacity, frequency of administration, formulation administered, elimination rate, and rate and/or degree of absorption from the route/site of administration.

Embodiments

As discussed above, mitochondrial fission is important in physiological and pathological processes. Such processes include coordination of mitochondrial and nuclear division during mitosis, and production of reactive oxygen species during cardiac ischemia-reperfusion injury. Mitochondrial fission is mediated by dynamin-related protein 1 (Drp1).

Results described herein show that compounds of Formula 1, below, are effective inhibitors of Drp1:

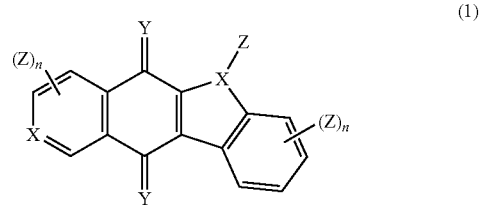

(1)

where X is N or C;
Y is O or S;
Z is a substituent that may be further substituted; and
n is 1-4, substituents comprise one or more moieties whose presence does not interfere with the desired reactivity and include alkyl, alkenyl, alkynyl, aryl, halide, heteroaryl, cyclyl (non-aromatic ring), Si(alkyl)$_3$, Si(alkoxy)$_3$, halo, alkoxyl, amino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfamoyl, sulfonamide, nitro, nitrile, azido, heterocyclyl, ether, ester, silicon-containing moieties, thioester, or a combination thereof. Table 1 shows embodiments of Formula 1 including a variety of substituents.

In particular, two representative examples of Formula 1 that are analogs of ellipticine were identified as specific Drp1 GTPase inhibitors that are more potent than standard Drp1 inhibitor mdivi-1. These two analogs, Drpitor1 and Drpitor1a (see Table 3), have utility through their inhibition of Drp1 and thereby reduction of mitochondrial fission. Accordingly, compounds of Formula 1 have therapeutic potential for treatment of cancer, pulmonary arterial hypertension, cardioprotection, Huntington's disease, Parkinson's disease, Alzheimer's disease and other conditions that are related to disorders of mitochondrial fission. Results described herein demonstrate efficacy of these potent Drp1 GTPase inhibitors.

In some embodiments of combination therapy, a first compound is of Formula (1). In other embodiments, the second compound is an antineoplastic agent that is not of Formula (1). Known antineoplastic agents that may be suitable in a combination therapy according to the invention include, but are not limited to anthracyclines (e.g., doxorubicin, daunorubicin), other antibiotic agents (e.g., the HSP90 inhibitor 17-AAG), Vinca alkaloids (e.g., vinblastine, vincristine), epipodophyllotoxins (e.g., etoposide, teniposide), pyrimidine analogs (e.g., gemcitabine, 5-fluorouracil, cytarabine), taxanes (e.g., paclitaxel), platinum-based cancer drugs (e.g., cisplatin), monoclonal antibodies (e.g., TZ/Herceptin), and equivalents thereof.

Compounds of the invention can be formulated to ensure proper distribution in vivo. For example, therapeutic compounds of the invention can be formulated in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade, V. V. J. Clin. Pharmacol. (1989) 29(8):685-94). Exemplary targeting moieties include folate and biotin (see, e.g., U.S. Pat. No. 5,416,016 to Low et al.); mannosides (Umezawa et al., Biochem. Biophys. Res. Commun. (1988) 153(3):1038-44; antibodies (Bloeman et al., FEBS Lett. (1995) 357:140; Owais et al., Antimicrob. Agents Chemother. (1995) 39(1):180-4); and surfactant protein A receptor (Briscoe et al., Am. J. Physiol. (1995) 268(3 Pt 1): L374-80). Liposomal formulations of Drp1 GTPase inhibitors may include a targeting moiety.

Delivery and in vivo distribution can also be affected by alteration of an anionic group of compounds of the invention. For example, anionic groups such as phosphonate or carboxylate can be esterified to provide compounds with desirable pharmacokinetic, pharmacodynamic, biodistributive, or other properties.

To administer a therapeutic compound by other than parenteral administration, it may be necessary to coat the compound with, or co-administer the compound with, a material to prevent its inactivation. For example, the therapeutic compound may be administered to a subject in an appropriate vehicle, for example, liposomes, or a diluent. Pharmaceutically acceptable diluents include saline and aqueous buffer solutions. Liposomes include water-in-oil-in-water CGF emulsions as well as conventional liposomes (Strejan et al., Prog. Clin. Biol. Res. (1984) 146: 429-34).

The therapeutic compound may also be administered ocularly, via inhalation, topically, intravaginally, as well as parenterally (e.g., intramuscularly, intravenously, intraperitoneally, intraspinally, intrathecally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g. vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

Solid dosage forms for oral administration include ingestible capsules, tablets, pills, lollipops, powders, granules, elixirs, suspensions, syrups, wafers, buccal tablets, troches, and the like. In such solid dosage forms the active compound is mixed with at least one inert, pharmaceutically acceptable excipient or diluent or assimilable edible vehicle such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the therapeutic compound in the compositions and preparations may, of course, be varied. The amount of the therapeutic compound in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Therapeutic compounds can be administered in time-release or depot form, to obtain sustained release of the therapeutic compounds over time. The therapeutic compounds of the invention can also be administered transdermally (e.g., by providing the therapeutic compound, with a suitable vehicle, in patch form).

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological conditions in subjects.

Therapeutic compounds according to the invention are administered at a therapeutically effective dosage sufficient to achieve the desired therapeutic effect, e.g. to prevent the spread of cancer and/or kill cancerous cells, to treatment and/or mitigate pulmonary arterial hypertension, cardioprotection, stroke, coronary heart disease, neurodegenerative diseases, Parksinonism, Huntington's Chorea, Alzheimer's disease, diabetic cardiomyopathy, fatty liver diseases, non-alcoholic fatty liver diseases, or alcohol-related liver disease. Actual dosage levels of active ingredients in the pharmaceutical compositions may be varied so as to obtain an amount of the active compound(s) that is effective to achieve and maintain the desired therapeutic response for a particular subject, composition, and mode of administration. The selected dosage level will depend upon the activity of the particular compound, the route of administration, frequency of administration, the severity of the condition being treated, the condition and prior medical history of the subject being treated, the age, sex, weight and genetic profile of the subject, and the ability of the therapeutic compound to produce the desired therapeutic effect in the subject. Dosage regimens can be adjusted to provide the optimum therapeutic response. For example, several divided doses may be administered daily or the dose may be proportionally reduced as indicated by the exigencies of the therapeutic situation.

However, it is known within the medical art to determine the proper dose for a particular patient by the dose titration method. In this method, the patient is started with a dose of the drug compound at a level lower than that required to achieve the desired therapeutic effect. The dose is then gradually increased until the desired effect is achieved. Starting dosage levels for an already commercially available therapeutic agent of the classes discussed above can be derived from the information already available on the dosages employed. Also, dosages are routinely determined through preclinical ADME toxicology studies and subsequent clinical trials as required by the FDA or equivalent agency. The ability of a Drp1 GTPase inhibitor to produce the desired therapeutic effect may be demonstrated in various models for the various conditions treated with these therapeutic compounds.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention will contain between 1 and 1000 mg, and usually between 5 and 500 mg, of at least one compound of the disclosure, e.g., about 10, 25, 50, 100, 200, 300 or 400 mg per unit dosage which can be administered as a single dose or divided into multiple doses.

As evidenced by Mordenti (*J. Pharm. Sci.* 1986 75(11): 1028-40) and similar articles, dosage forms for animals such as, for example, rats can be and are widely used directly to establish dosage levels in therapeutic applications in higher mammals, including humans. In particular, the biochemical cascade initiated by many physiological processes and conditions is generally accepted to be identical in mammalian species (see, e.g., Mattson et al. Neurotrauma 1994 11(1): 3-33; Higashi et al. Neuropathol. Appl. Neurobiol. 1995 21:480-483). Accordingly, pharmacological agents that are efficacious in animal models such as those described herein are believed to be predictive of clinical efficacy in humans, after appropriate adjustment of dosage.

According to the FDA, calculating a human equivalent dose from animal studies needs to done by normalizing to bovine serum albumin (Center for Drug Evaluation and Research, Center for Biologics Evaluation and Research. (2002) *Estimating the safe starting dose in clinical trials for therapeutics in adult healthy volunteers*, U.S. Food and Drug Administration, Rockville, Md., USA). This can be done using $K_m$ factors where the Human equivalent dose (HED)=animal dose in mg/kg multiplied by animal Km/human $K_m$ (Reagan-Shaw et al. FASEB J. 2008 March; 22(3): 659-61). The HED for a dose of 0.05 mg/kg in a mouse is equal to 0.05 mg/kg×3/37=0.004 mg/kg in a human.

Potential inhibitors were identified using in silico screening. Virtual screening was performed to identify compounds having a high predicted binding affinity for Drp1's GTPase domain. Compounds with high predicted affinity to Drp1 GTPase domain then underwent in vitro screening (see Table 1 for structural formulae of the screened compounds and Example 1 for screening details).

One compound, Drpitor1 (see Table 3 for structural formulae), inhibited mitochondrial fission as well as standard mdivi-1, but at a lower dose (0.6 µM vs 20 µM, respectively). An amine derivative of Drpitor1, known herein as Drpitor1a (see Table 3 for structural formulae), was synthesized as described in Example 3 and was also studied (see Figures and Table 3).

Validation of potential inhibitors was performed by in vitro and in vivo studies and results were compared to standard Drp1 inhibitor, mdivi-1. Candidate molecules with high binding affinities were screened for their ability to inhibit Drp1 GTPase activity. A cell line was used for these studies. Specifically, A549 cells, which are adenocarcinomic human alveolar basal epithelial cells, were studied. In these studies, which are described herein, specificity of compounds for Drp1 versus another large GTPase (i.e., dynamin 1) was assessed. Mitochondria were visualized in live A549 cancer cells by confocal microscopy using TMRM. Mitochondrial fission was quantified by measurement of mitochondrial fragmentation count (MFC) and by a machine learning algorithm. Anti-proliferative effects of certain compounds were assessed in vitro in cancer cells and in vivo via a murine xenotransplantation cancer model. Further, as described herein, Drp1 inhibitors of Formula 1 are effective at cardioprotection. As discussed in Example 8, treatment was assessed using ischemia-reperfusion injury in a rodent right ventricular Langendorff model.

Details are also provided herein regarding demonstration that Drpitor1 and Drpitor1a had inhibitory effects on Drp1 GTPase activity. The compounds inhibited mitochondrial fission, cell proliferation, and induced apoptosis. Demonstration of the therapeutic efficacy of Drpitor1a was obtained in a xenograft murine model of lung cancer showing that it occurred without inducing hepatic or renal toxicity. Evaluation of a Drp1-mediated cardioprotective effect of Drpitor1a was observed in a RV-IR model. Notably, Drpitor1a reduced ROS production and was cardioprotective.

As shown in the figures, mitochondrial fission was inhibited by Drpitor1 and Drpitor1a in lung and breast cancer cell lines and PAH PASMC cell lines, as shown by decreased MFC and increased percentage of elongated, filamentous mitochondria. Dripitor-mediated fusion was mediated by inhibition of Drp1 GTPase activity. Drpitor1a inhibited cell proliferation and induced apoptosis in lung and breast cancer cell lines, PAH PASMC cell lines and brain tumor cell lines and suppressed tumor growth in a mouse xenograft lung cancer model. Drpitor1a also reduced mitochondrial ROS and prevented right ventricular diastolic dysfunction during cardiac ischemia-reperfusion injury in a rat model.

Drpitor1 and Drpitor1a were tested in two distinct fissogenic conditions, a hyperproliferative disease marked by increased mitotic fission (cancer) and a cell injury model, in which fission causes cell injury through ROS production. Drp1 is a key regulator of mitochondrial fission and its activation during mitosis ensures equitable distribution of mitochondria to daughter cells. Mitotic mitochondrial fission is inhibited by molecular silencing (by siRNA) or pharmacological inhibition (by small compound mdivi-1) of Drp1, which leads to cell cycle arrest and apoptosis. Mitochondrial fission is also critical to a pathologic process, cardiac IR injury, which is commonly seen in subjects with myocardial infarction receiving revascularization treatments. In animal models of pulmonary arterial hypertension, IR is seen in the RV and this RV-IR injury results in a deleterious increase in ROS production and calcium overload. Inhibition of Drp1 activity or the interaction between Drp1 and its binding partner Fis1 is cardioprotective during experimental IR.

Referring to FIG. 1, a bar graph is shown depicting mitochondrial fragmentation count (MFC) of test compounds on A549 cells showing significant inhibition of mitochondrial fragmentation achieved by compound #12, which is referred to herein as Drpitor1, and compound #13 (see Table 1), treatment.

Figure 2:
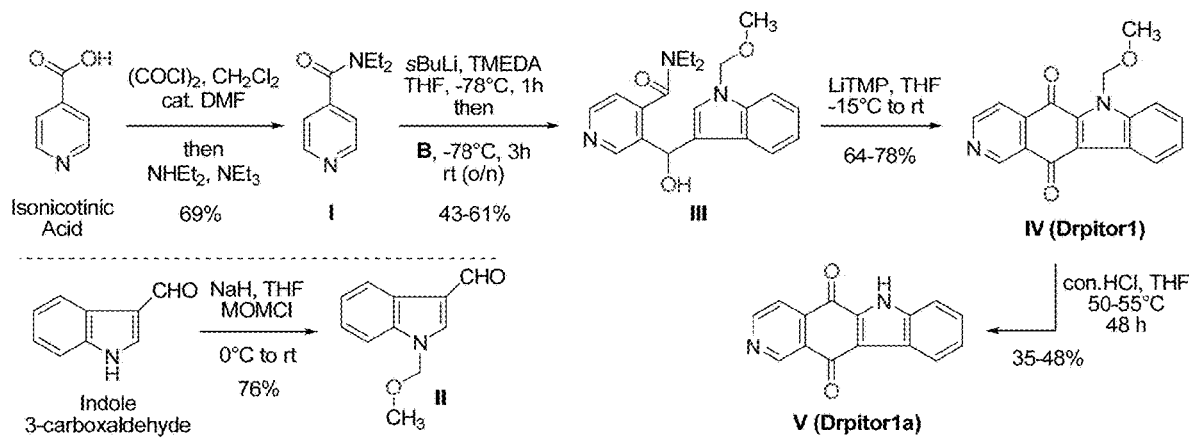

Referring to FIG. 2, a synthetic route is shown to Drpitor1 and Drpitor1a. Final compound Quinone E was prepared with a modification of an earlier report (Watanabe M. et al., *J. Am. Chem. Soc.* 1980; 102:1457-1460.). Quinone Drpitor1a was prepared from iso-nicotinamide (I) and indole 3-carboxaldehyde (II) using a modified procedure. Thus lithiation of Compound (I) with s-BuLi under standard conditions followed by quench with aldehyde (II) gave carbinol intermediate III (43-61% yield). Compound (III) was further subjected to lithiation and an intramolecular cyclization sequence followed by aerial oxidation which occurred upon work-up to give methoxymethyl (MOM) protected quinone (IV) ("Drpitor1") in 64-78% yield. The deprotection of MOM group with con. HCl afforded final quinone (V) ("Drpitor1a") in in low yield.

Figure 3A:
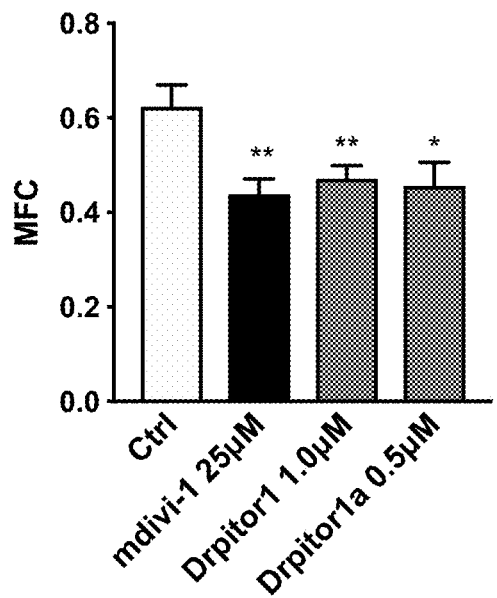
FIG. 3A is a bar graph depicting MFC vs treatment, wherein significantly reduction of MFC was shown for all agents relative to control, n=15-20 per group; *$P<0.05$ vs Ctrl, **$P<0.01$ vs Ctrl.
Figure 3B:
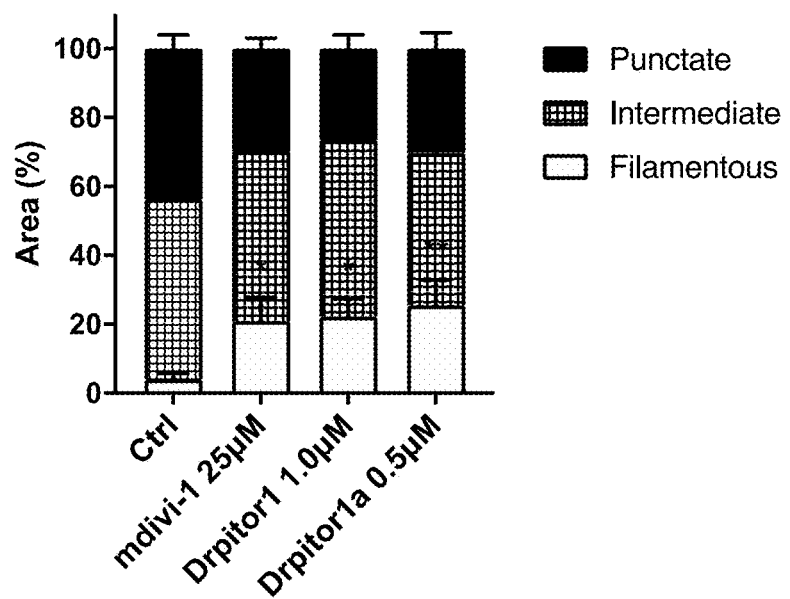
FIG. 3B is a bar graph of percentage area of different shapes of mitochondria vs. treatment, wherein percentage of filamentous mitochondria was significantly increased for all agents relative to control, n=15-20 per group; *$P<0.05$ vs Ctrl, **$P<0.01$ vs Ctrl.

Referring to FIG. 3A, a bar graph is shown depicting MFC vs treatment, wherein significantly reduction of MFC was shown for all agents relative to control. Referring to FIG. 3B, a bar graph is shown of percentage area of different shapes of mitochondria vs. treatment, wherein percentage of filamentous mitochondria was significantly increased for all agents relative to control. The results shown in FIGS. 3A and 3B provide evidence of reduction of mitochondrial fission.

Figure 4A:
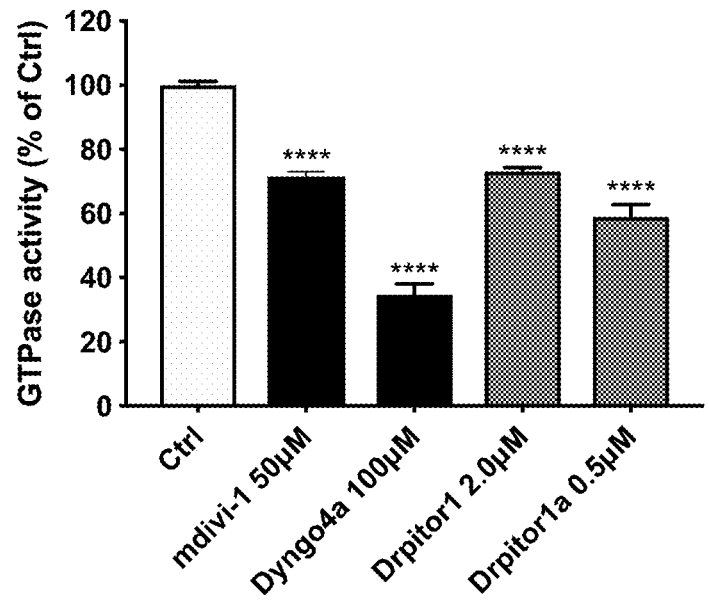
FIG. 4A is a bar graph depicting GTPase activity of Drp1 in A549 cells vs. treatment, wherein a significant decrease is shown for treatment with mdivi-1 (50 μM) (positive control), Dyngo4a (100 μM) (positive control), Drpitor1 (2.0 μM) or Drpitor1a (0.5 μM) for 6 hours, n=3 per group; ****$P<0.0001$ vs Ctrl.

Referring to FIG. 4A, a bar graph is shown that depicts GTPase activity of Drp1 in A549 cells vs. treatment, wherein a significant decrease is shown for treatment with mdivi-1, Dyngo4a, Drpitor1, or Drpitor1a for 6 hours.

Figure 4B:
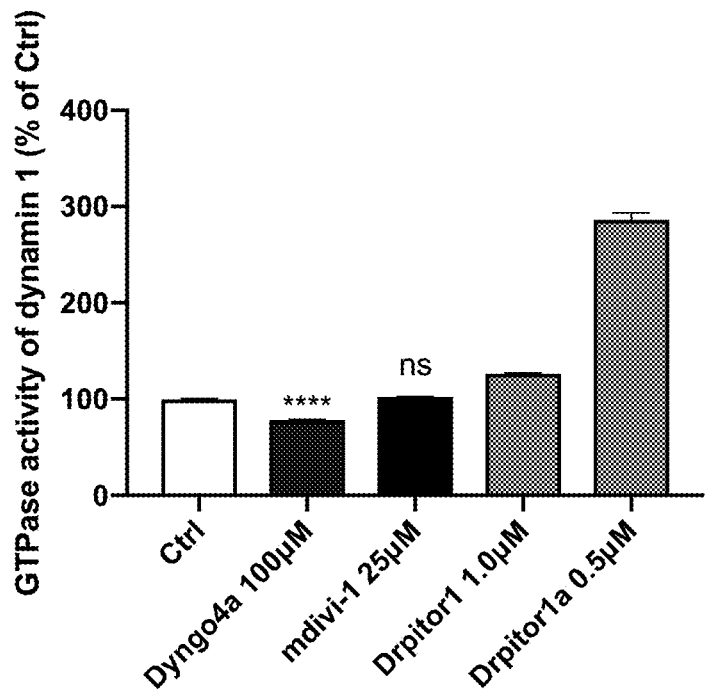
FIG. 4B is a bar graph depicting GTPase activity of dynamin 1 in A549 cells vs. treatment, wherein a significant decrease was seen for treatment with Dyngo4a (100 μM) (positive control), which was not seen for treatment with mdivi-1 (25 μM), Drpitor1 (1.0 μM) and Drpitor1a (0.5 μM), n=3 per group; ****$P<0.0001$ vs Ctrl, ns, not significant.

Referring to FIG. 4B, a bar graph is shown that depicts GTPase activity of dynamin 1 in A549 cells vs. treatment, wherein a significant decrease was seen for treatment with Dyngo4a, which was not seen for treatment with mdivi-1, Drpitor1 or Drpitor1a.

Figure 5A:
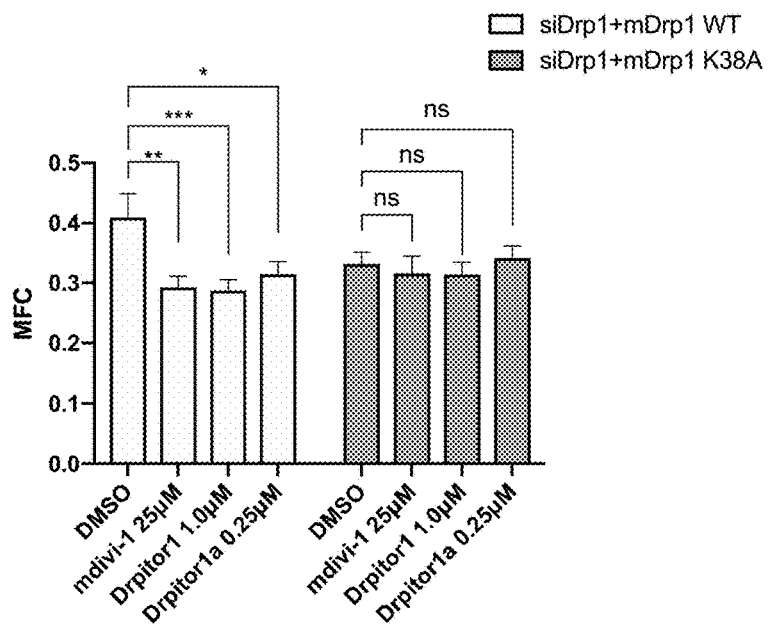
FIG. 5A is a bar graph depicting MFC versus treatment, wherein a significantly reduction was seen for mdivi-1, Drpitor1 and Drpitor1a treatment in cells transfected with siDrp1+mDrp1 WT, but this reduction was not seen in cells transfected with siDrp1+mDrp1 K38A. n=15-20 per group; *$P<0.05$, $P<0.01$, *$P<0.001$, ns, not significant.

Referring to FIG. 5A, a bar graph is shown depicting MFC versus treatment, wherein a significantly reduction was seen for mdivi-1, Drpitor1 and Drpitor1a treatment in cells transfected with siDrp1+mDrp1 WT, but this reduction was not seen in cells transfected with siDrp1+mDrp1 K38A.

Figure 5B:
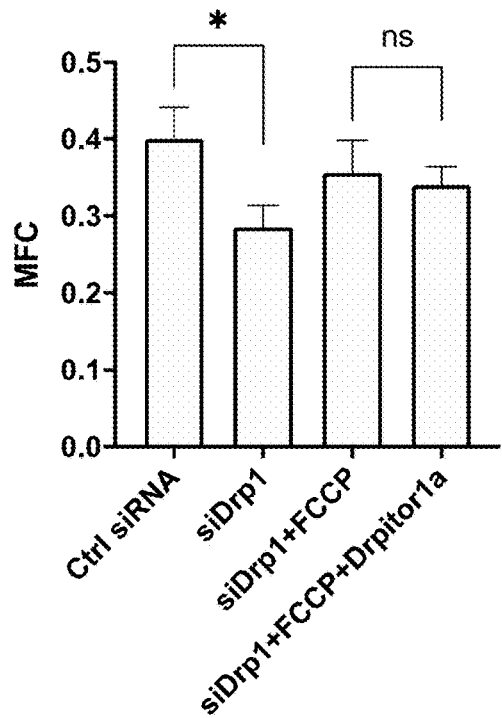
FIG. 5B is a bar graph depicting MFC of A549 cells versus treatment, wherein a significant reduction was seen for siDrp1 treatment, and an increase of MFC was seen for siDrp1+FCCP treatment, but reduction of MFC was not seen for adding Drpitor1a to siDrp1+FCCP treatment. n=12-15 per group; *$P<0.05$, ns, not significant.

Referring to FIG. 5B, a bar graph is shown depicting MFC vs. treatment, wherein a significant reduction was seen for siDrp1 treatment, and an increase of MFC was seen for siDrp1+FCCP treatment, but reduction of MFC was not seen for adding Drpitor1a to siDrp1+FCCP treatment.

Figure 5C:
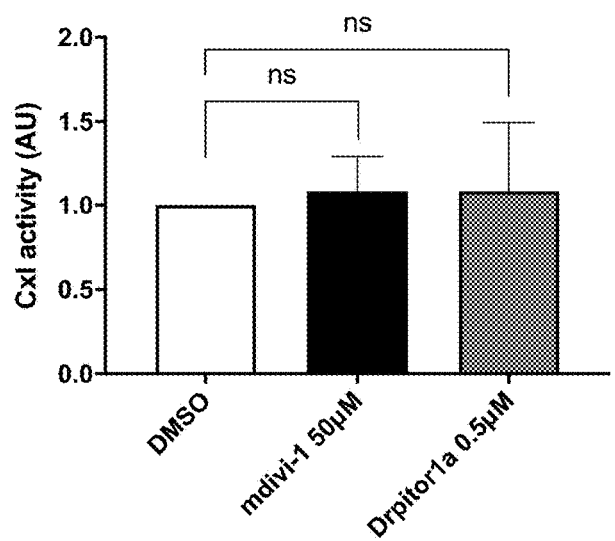
FIG. 5C is a bar graph depicting mitochondrial complex I activity in A549 cells vs. treatment, wherein no significant change was seen for treatment with mdivi-1 (50 μM) or Drpitor1a (0.5 μM). n=3 per group; ns, not significant.

Referring to FIG. 5C, a bar graph is shown depicting mitochondrial complex I activity in A549 cells vs. treatment, wherein no significant change was seen for treatment with mdivi-1 (50 µM) or Drpitor1a (0.5 µM).

Figure 6A:
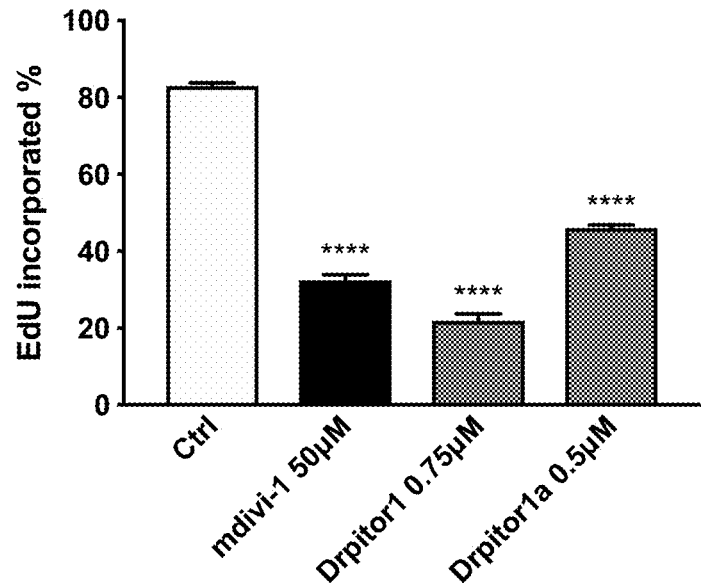
FIG. 6A is a bar graph of percentage of cells that has EdU incorporated into their DNA vs. treatment as indicted, wherein the percentage of EdU incorporated cells was significantly reduced after treatment with mdivi-1 (50 μM) (positive control), Drpitor1 (0.75 μM) or Drpitor1a (0.5 μM), n=3-6 per group; ****$P<0.0001$.
Figure 6B:
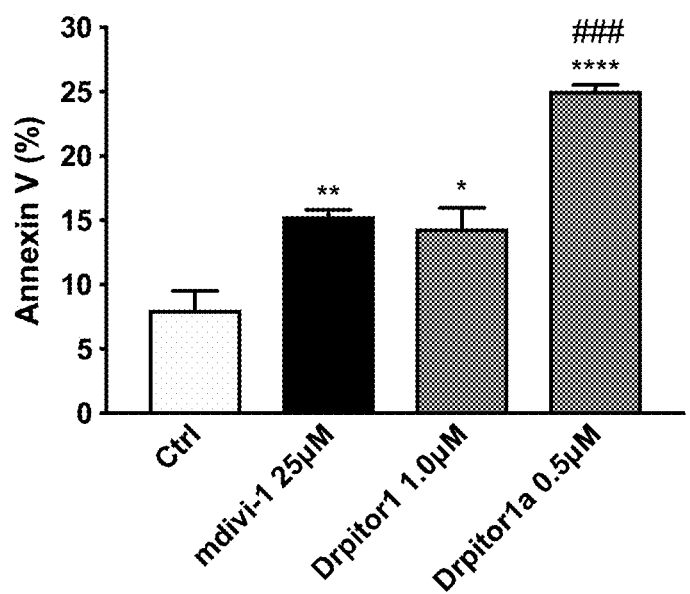
FIG. 6B is a bar graph of percentage of cells with positive Annexin V staining vs. treatment, wherein a baseline apoptosis rate was significantly higher in A549 cells treated with mdivi-1 (25 μM) (positive control), Drpitor1 (1.0 μM) or Drpitor1a (0.5 μM) relative to control, n=3 per group; $P<0.01$, **$P<0.0001$.

Referring to FIG. 6A, results are shown that indicate percentage EdU positive cells was significantly reduced after treatment with Drpitor1 (0.75 µM) or Drpitor1a (0.5 µM). Referring to FIG. 6B, results are shown that indicate baseline apoptosis rate was significantly higher in A549 cells treated with Drpitor1 (1.0 µM) or Drpitor1a (0.5 µM).

Figure 7A:
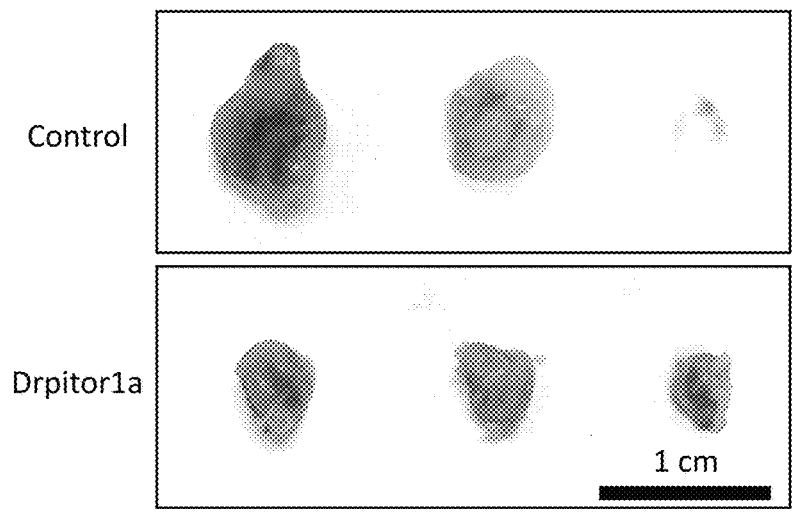
FIG. 7A shows representative images of decreased tumor size in the Drpitor1a-treated group compared to control group. Scale bar=1 cm.
Figure 7B:
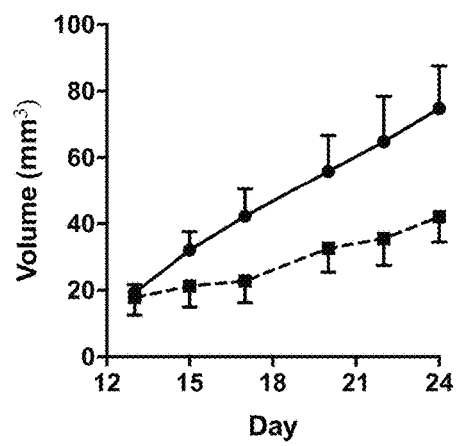
FIG. 7B is a graph of tumour volume vs. number of days post tumour cell introduction (treatment started on Day 2) and indicates that the tumor growth rate was lower in the Drpitor1a treated group.
Figure 7C:
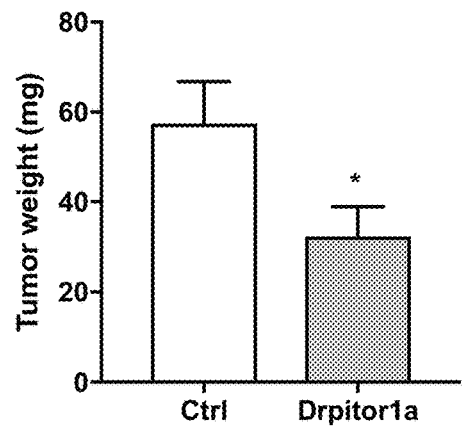
FIG. 7C is a bar graph of tumour weight vs. treatment for Drpitor1a-treated group and controls, wherein a significant reduction in tumor weight was seen compared to the control group. n=12 for Ctrl, n=7 for Drpitor1a; *$P<0.05$.

Referring to FIGS. 7A to 7C, results are shown that indicate decreased tumor size, lower tumour growth rate, and reduction in tumour weight in the Drpitor1a-treated group compared to control group.

Referring to FIGS. 8A-D, results are shown that indicate prevention of RV ischemia-reperfusion (IR) injury by Drpitor1a. These results provide evidence of cardioprotective effects. In one study, Drpitor1a-treated hearts did not manifest the increase in RVEDP that was seen in control hearts, which were treated with DMSO, after two periods of ischemia-reperfusion challenge.

The following working examples further illustrate the invention and are not intended to be limiting in any respect.

Working Examples

Methods

Cell Culture: A549 cells were purchased from the American Type Culture Collection (ATCC) and were cultured in Dulbecco's Modified Eagle's Medium (DMEM) (D5796, Sigma Aldrich) supplemented with 10% fetal bovine serum (FBS). Cells were cultured at 37° C. in a humidified incubator balanced with 5% $CO_2$.

Compound solution preparation for in vitro experiments: Candidate compounds were dissolved in anhydrous Dimethyl Sulfoxide (DMSO) (available from Sigma Aldrich), filtered by a 0.20 µm PTFE filter and added to culture medium to make a working solution at designated concentrations. Final concentration of DMSO in culture medium was s 0.1%. Same volume of DMSO was used as control.

Mitochondrial morphology analysis: Mitochondrial morphology of live cells was analyzed 4 hours post compound treatment. Two objective methods were used to examine mitochondrial morphology: 1) MFC; 2) a machine-learning approach measuring the percentage area of punctate, intermediate or filamentous mitochondria. For MFC calculation and machine-learning algorithm, cells were loaded with 20 nM TMRM prior to confocal microscopy using Leica SP8 confocal microscope. Mitochondrial images were taken under a 1.40 NA, ×63 oil immersion objective with ×3 digital zoom using the Leica LAS X software (λex/em=561/>575 nm). All images were taken by the same microscopist who was blinded to the treatment groups. MFC and the percentage area of punctate, intermediate or filamentous mitochondria were analyzed. Briefly, MFC was calculated as the total mitochondrial number divided by the total mitochondrial area in each confocal microscopy image. Higher MFC indicates more fragmented mitochondrial network. Percentage area of punctate, intermediate or filamentous mitochondria were analyzed by a machine learning algorithm (Chen K. H., et al., Circulation. 2018). Punctate, intermediate and filamentous mitochondria were classified manually by the morphology followed by a machine learning algorithm based on the area, length, sphericity of the mitochondria. The percentage area of each category in each confocal image was calculated and the distribution of three categories was compared among groups.

Immunoprecipitation of Drp1: A549 cells were pretreated with candidate compounds for 20 hours and total protein was extracted by Cell Lysis Buffer (9803, Cell Signaling Technology) followed by sonication. A total of 800 µg of whole cell extract from each group was allowed to bind to 2 µg of total Drp1 antibody (611112, BD Transduction Laboratories) at 4° C. for 5 hours followed by immunoprecipitation with 50 µL of protein A/G-agarose beads (sc-2003, Santa Cruz Biotechnology) at 4° C. overnight.

Immunoprecipitation of dynamin 1: A549 cells were transfected with 2.5 µg of WT HA-dynamin 1 (34682, Addgene) plasmid. Candidate compounds were added to cells 48 hours post transfection and cells were collected after 20 hours of compound treatment. Total protein was extracted by Cell Lysis Buffer (9803, Cell Signaling Technology). A total of 500 µg of whole cell extract from each group was immunoprecipitated with 10 µL of HA-tag antibody (3724, Cell Signaling Technology, Inc.) at 4° C. for 5 hours. Then the protein-antibody was incubated with 50 µL of protein A/G-agarose beads (sc-2003, Santa Cruz Biotechnology) at 4° C. overnight. An empty vector containing HA-tag (pCGN plasmid) was used as negative control.

GTPase activity assay: After incubation with protein-antibody mixture, the protein A/G-agarose beads were centrifuged and washed twice with RIPA Lysis and Extraction Buffer (available from ThermoFisher Scientific) and twice with GTPase buffer (50 µM Tris-HCl pH 7.5, 2.5 µM $MgC_2$), then incubated with 0.5 mM GTP at 30° C. for 30 minutes. The released free phosphate was quantified using the High Throughput Colorimetric GTPase assay kit (available from Innova Biosciences Ltd) according to manufacturer's protocol. $OD_{620}$ was measured by a SpectraMax M3 microplate reader (Molecular Devices).

Cell transfection: A549 cells were seeded in 35 mm glass bottom dishes (available from MatTek Corporation) at a density of $3-4 \times 10^4$/dish. Drp1 was first knocked down with small interfering RNA against Drp1 (sense: 5'-CCC-UAGCUGUAAUCACUAAACUUGA-3' (SEQ ID NO: 1), anti-sense: 3'-UUGGGAUCGA-CAUUAGUGAUUUGAACU-5' (SEQ ID NO: 2), Integrated DNA Technologies, Inc., Coralville, Iowa, USA). After 24 hours of knockdown, wildtype mouse Drp1 plasmid or mutant mouse Drp1 at K38A plasmid was overexpressed in these dishes. Compounds were added 48 hours post plasmid overexpression and images were taken 4 hours post compound treatment.

Cell proliferation assay: Cell proliferation was measured 48 hours post compound treatment using Click-iT® EdU Alexa Fluor® 488 Imaging Kit (available from Thermo Fisher Scientific) according to manufacturer's protocol. $1.0 \times 10^5$ cells were seeded per well in 6-well plates and compounds were added 24 hours after seeding. EdU was allowed to incorporate 10 hours before flow cytometry. Percentage of cells incorporated with EdU in each group was determined using SONY SH800S flow cytometer and compared between control group and treatment groups.

Apoptosis assay: Cell apoptosis was determined by the Annexin V+ propidium iodide (PI) method using Alexa Fluor 488 Annexin V/Dead Cell Apoptosis Kit (available from ThermoFisher Scientific). A549 cells were collected 48 hours after compound treatment. Percentage of Annexin V (+) and PI (+) cells was determined using SONY SH800S flow cytometer and compared between control group and treatment groups.

Colony formation assay: Cells were seeded in 6-well plates and optimal concentrations of compounds were added 24 hours after seeding. After 48 hours of compound treatment, cells were disassociated with 0.25% trypsin-EDTA (25200114, Gibco, Burlington, ON, Canada) and reseeded in a 48-well plate at a density of 200 live cells/mL. After 7-10 days of culture, cells were fixed with 4% paraformaldehyde and then stained with 1% crystal violet (V5265, Millipore Sigma, Etobicoke, ON, Canada). Images of cell colonies were taken by a Panasonic LX3 digital camera (Kadoma, Osaka, Japan).

In vivo xenotransplant tumor model: BALB/c Rag2$^{-/-}$; IL2Rgc$^{-/-}$ double knock out mice were kindly provided by Dr. M Ito, Central Institute for Experimental Animals, Kawasaki, Japan and were bred in the Animal Facility at Queen's University. Animal protocols were approved by the University Animal Care Committee of Queen's University. A xenotransplant mouse model of human lung cancer was established by subcutaneous injection of A549 cells (4.0× $10^1$ per tumor) at the back flank regions. Drpitor1a was dissolved in DMSO and mice were treated with 10 mg/kg body weight with intraperitoneal injections three times a week starting at day 2. Equal volumes of solvents were injected as control. When tumors reached ~5 mm diameter, intratumoral injection of Drpitor1a was administered three times a week. Tumor length and width was measured every 2 days. Animals were euthanized with cervical dislocation under 5% isoflurane inhalation followed by tumor collection. Blood samples were collected for liver and kidney toxicity studies just before euthanasia.

Langendorff right ventricle ischemia-reperfusion (RV-IR) model: The Langendorff RV-IR experiment was performed as previously described (Tian L., et al., *J. Mol. Med.* (Berl). 2017 95(4): 381-393). Briefly, Sprague-Dawley rats were anesthetized with an intraperitoneal injection of ketamine (75 mg/kg)/xylazine (10 mg/kg). The hearts were harvested and perfused with oxygenated Krebs' solution at 37° C. at a constant pressure of 85 cmH$_2$O on a Langendorff apparatus. RV pressure was measured by a fluid-filled balloon placed in the RV connected to a pressure transducer (Harvard Apparatus; Holliston, Mass., USA). High fidelity signals were recorded using PowerLab 8/35 data acquisition hardware and analyzed using LabChart Pro 8 software (AD Instruments; Colorado Springs, Colo., USA).

IR protocol: Hearts were stabilized for 10 minutes before the IR experiment. Two consecutive cycles of 20 minutes of global ischemia followed by 20 minutes of reperfusion were performed. Drpitor1a (0.5 µM) was added to the perfusate ~10 minutes before the first ischemia. Same volume of DMSO was used as a negative control for test compound. Right ventricular myocardium was collected at the end of RV-IR for the measurement of mitochondrial superoxide and mitochondrial morphology.

Mitochondrial superoxide imaging and quantification: RV tissues collected from Langendorff RV-IR experiments were cut into pieces of 1×1×1 mm$^3$ and were incubated with 5 µM of MitoSOX™ Red mitochondrial superoxide indicator (available from Molecular Probes™) at 37° C. for 15 minutes. Tissues were then washed three times with HBSS/ Ca/Mg buffer before being imaged. Images of RV tissues were taken by a 2-photon microscope (Leica TCS SP8 Confocal, Leica System) using a 0.85 NA, 40× objective and 0.75× digital zoom. Specifications for the 2-photon laser include: 1.44 W at intensity 15.8% (λex/em=775/580 nm). All images were taken by the same microscopist who was blinded to the treatment groups. Intensity of the MitoSOX™ Red mitochondrial superoxide indicator was analyzed by the Leica LAS X software.

Statistical analyses: Quantitative data are presented as mean standard error of mean (SEM). Student's t-test or Mann-Whitney U test was used to compare the mean or median value between two groups as appropriate. One-way ANOVA was used to compare the means of three or more independent groups. Two-way ANOVA was used to compare the mean differences between groups that have two independent variables. A P-value of less than 0.05 was considered statistically significant.

Example 1. In Silico Chemical Screen for Drp1 GTPase Inhibitor

Virtual screening was completed using the published crystal structures for Drp1 (4H1V) and dynamin 1 (5D3Q) with the screening software PyRx 0.9.1. A proprietary chemical compound library of over 4,000 compounds was used. The compounds, in .sdf file format, were converted to pdbqt file format by Open Babel in PyRx as ligands for virtual screening.

A proprietary chemical compound library of over 4,000 compounds was used for in silico screening. Virtual screening identified compounds that have specific binding affinities against the GTPase domain of Drp1 protein (PDB ID: 4H1V, https://www.rcsb.org/structure/4H1V). Another large GTPases with similar structure, dynamin 1 (PDB ID: 5D3Q, https://www.rcsb.org/structure/5d3q), was used as a negative control to identify the specificity of compounds against Drp1. For screening, catalytic site residues were selected based on published crystal structures and made flexible for virtual screening. For Drp1, residues included Gln34, Ser35, Lys38, Ser39, Ser40, Arg53, Thr59, Asp146, Gly149, Lys216, Asp218, and Asn246. For dynamin 1, residues included Ser45, Arg59, Ser61, Thr65, Asp136, Asp208, Asn236, and Gln239. The screening grid was minimized to contain the flexible residues. After in silico screening, seventeen compounds were selected based on their predicted binding affinities to Drp1 for in vitro screening (see Table 1).

Example 2. Identifying the Compound of Interest (Drpitor1) by In Vitro Screening Inhibitory effect of compounds on Drp1 GTPase activity was studied in the A549 human non-small cell lung cancer (NSCLC) cell line. These cells have a fragmented mitochondrial network due to increased Drp1 expression and activity, relative to normal airway epithelial cells. Mitochondrial morphology was used as an indicator of Drp1 activity in the in vitro screening, such that Drp1 inhibitors would be identified by an increase in fusion. Out of the 17 compounds screened, compounds #12 (Drpitor1) and #13 (see Table 1) showed the most significant inhibition of mitochondrial fission, evident as a reduction in mitochondrial fragmentation count (MFC), a validated quantitative measurement of mitochondrial fragmentation. However, the concentration of Drpitor1 (5H,5aH,6H,10bH,11H-pyrido[4,3-b] carbazole-5, 11-dione, analog of ellipticine) was much lower than that of compound #13 (0.6 µM vs 20 µM). Thus, Drpitor1, which was predicted to be a kinase or enzyme inhibitor (see Table 2), was selected for further investigation. Prediction of oral availability showed it does not violate Lipinski's rule of 5, which indicates it is potentially orally active (Lipinski C. A., et al., *Adv. Drug Deliv. Rev.* 2001; 46:3-26).

Example 3. Synthesizing a Stable and Potent Analogue of Drpitor1 (Drpitor1a)

Because the methoxymethyl group of compound Drpitor1 is predicted to be hydrolytically labile, an analogue compound having an amine instead of a methoxymethyl group was synthesized (Drpitor1a, see FIG. 2). FIG. 2 depicts synthetic route to Drpitor1a. Lithiation of compound I (see FIG. 2) with s-BuLi under standard conditions followed by quench with aldehyde II gave carbinal intermediate III (43-61% yield). Compound III was further subjected to lithiation and an intramolecular cyclization sequence followed by aerial oxidation which occurred upon work-up to give methoxymethyl protected quione IV (Drpitor1) in 64-78% yield. Deproptection of methoxymethyl with conc. HCl afforded Drpitor1a.

Similar to Drpitor1, Drpitor1a is expected to have at least one log order higher binding affinity to Drp1 than mdivi-1 (Drpitor1 vs mdivi-1: −8.4 vs −7.2; Drpitor1a vs mdivi-1: −9.1 vs −7.2, Table 3) and to be an enzyme inhibitor (Table 2). Interaction between Drpitor1 or Drpitor1a with the GTPase domain of Drp1 was investigated as described in Example 1. Comparing the predicted binding location of these new compounds and mdivi-1 to Drp1-crystal bound GTP analog Guanylyl-imidodiphosphate (GMP-PNP) suggests the binding is occurring in the phosphate-binding region of the binding cavity, i.e., the GTPase domain of Drp1. We proceeded the subsequent in vitro experiments with both Drpitor1 compounds.

Example 4. Drpitor1 and Drpitor1a Inhibit Mitochondrial Fission

Drpitor1 (1.0 µM) and Drpitor1a (0.5 µM) both significantly inhibited mitochondrial fission in various hyperproliferative cells, including lung cancer cells (A549, SK-MES-1, SK-LU-1, SW 900), breast cancer cells (MCF7), PASMC from patients with PAH, as shown by elongated mitochondrial network. A significant decrease in MFC proved the inhibition of mitochondrial fragmentation in Drpitor-treated cells (FIG. 3A, Table 4, Table 9). Drpitor1 and Drpitor1a increased percentage area of elongated mitochondria, as measured by an unbiased machine learning technique (FIG. 3B). Although mdivi-1, showed the same degree of inhibition of mitochondrial fission in A549 cells, the potency of the Drpitor compounds was much greater (Drpitor1: 1 µM, Drpitor1a: 0.5 µM, mdivi-1: 25 µM). This is likely due to their predicted higher binding affinity to Drp1 than mdivi-1 (Drpitor1: −8.4, Drpitor1a: −9.1 versus mdivi-1: −7.2)(see Table 3).

Example 5. Drpitor1 and Drpitor1a are Specific Drp1 GTPase Inhibitors

To investigate whether the observed Drpitor-induced mitochondrial fusion results from inhibition of the Drp1 GTPase domain, total Drp1 from A549 cells treated with Drpitor1 or Drpitor1a was immunoprecipitated and Drp1 GTPase activity was measured. Drpitor1 (2.0 µM) and Drpitor1a (0.5 µM) both significantly inhibited the GTPase activity of Drp1 (see FIG. 4A) without changing the expression levels of total Drp1.
To determine that the specificity of these new compounds, we evaluated their ability to inhibit the GTPase activity of dynamin 1. Hemagglutinin (HA)-tagged dynamin 1 were immunoprecipitated from A549 cells transfected with HA-tagged dynamin 1 plasmid and treated with Drpitor1 or Drpitor1a. Drpitor1 (1.0 µM) and Drpitor1a (0.5 µM) did not inhibit the dynamin1 GTPase activity (FIG. 4B) nor did they alter dynamin expression in A549 cells.

The test compounds' effect on the Drp1 GTPase domain was tested. In order to prove that Drp1 is the only target for the Drpitors, endogenous Drp1 was first knocked down in A549 cells using siRNA and then restored by transfection with either a wildtype mouse Drp1 plasmid or a mutant mouse Drp1 plasmid (K38A), in which lysine 38 is substituted by alanine, resulting in a non-functional GTPase. Drpitor1 (1.0 µM) and Drpitor1a (0.25 µM) significantly inhibited mitochondrial fission in siDrp1-treated wildtype Drp1-rescued A549 cells (FIG. 5A). However, in cells transfected with in siDrp1 and mutant Drp1 plasmid, the mitochondrial network was fused and could not be further elongated by Drpitor1 or Drpitor1a treatment, reflecting the loss of the target that these compounds act on, namely, a functioning Drp1.

To overcome the problem of a maximally fused mitochondrial network, caused by Drp1 knockdown, fission was induced by a Drp1-independent mechanism. Carbonyl cyanide-4-(trifluoromethoxy) phenylhydrazone (FCCP) was added, a mitochondrial oxidative phosphorylation uncoupler, to cells treated with siDrp1. FCCP caused mitochondrial fission in Drp1 knocked-down A549 cells in a Drp1-independent manner19 (FIG. 5B). Drpitor1a (0.25 µM) did not rescue mitochondrial fission in these FCCP-treated Drp1 knocked-down cells (FIG. 5B), further indicating that the inhibition of mitochondrial fission by Drpitor1a is solely Drp1 dependent.

Although a previous study demonstrated that mdivi-1 can inhibit mitochondrial complex I activity (Bordt E. A., et al., *Dev Cell*. 2017; 40:583-594 e6), neither mdivi-1 nor Drpitor1a (0.5 µM) changed the mitochondrial complex I activity in A549 cells (FIG. 5C).

Taken together, these results indicate that Drpitor1 and Drpitor1a cause fusion by their actions as specific Drp1 GTPase inhibitors.

Example 6. Drpitor1 and Drpitor1a Inhibited Cell Proliferation and Induced Apoptosis Both Drpitor1 and Drpitor1a significantly inhibited cell proliferation in A549 cells after 48 hours of treatment (FIG. 4A). Drpitor1a inhibited proliferation of lung cancer (SK-MES-1, SK-LU-1, SW 900), breast cancer (MCF7) and brain cancer (Daoy, U373, U87) (Table 5, Table 11). Drpitor1a also inhibited cell proliferation of PASMC from PAH, a benign proliferative disease (Table 10). The effect of Drpitor1a on cell proliferation is dose-dependent. Colony formation assay indicated that Drpitor1a inhibited cell survival in A549, SK-MES-1, SK-LU-1, SW 900, and MCF7 cell lines (Table 6). Furthermore, both Drp1 inhibitors increased unstimulated apoptosis in A549 cells, as shown by a significant increase in the percentage of cells with positive Annexin V staining after 48 hours of treatment (FIG. 4B). Drpitor1a also induced unstimulated apoptosis in SK-MES-1, SK-LU-1, and SW 900 cell lines (Table 7).

Example 7. Drpitor1a Inhibits Tumor Growth in a Mouse Xenograft Model

In order to evaluate the antiproliferative effect of Drpitor1a in vivo, a xenograft model of lung cancer was developed in immunocompromised mice. After the subcutaneous injection of tumor cells into the immunocompromised mice, Drpitor1a (10 mg/kg) was injected intraperitoneally and intratumorally. By the end of the study, Drpitor1a had significantly inhibited tumor growth by 43.8% reduction in tumor volume and 43.9% reduction in tumor weight (FIG.

7C). Drpitor1a did not reduce body weight, change tumor density or result in liver or kidney toxicity during 22 days of therapy (Table 8).

Example 8. Drpitor1a Preserves RV Diastolic Function in an RV-IR Model

Figure 8A:
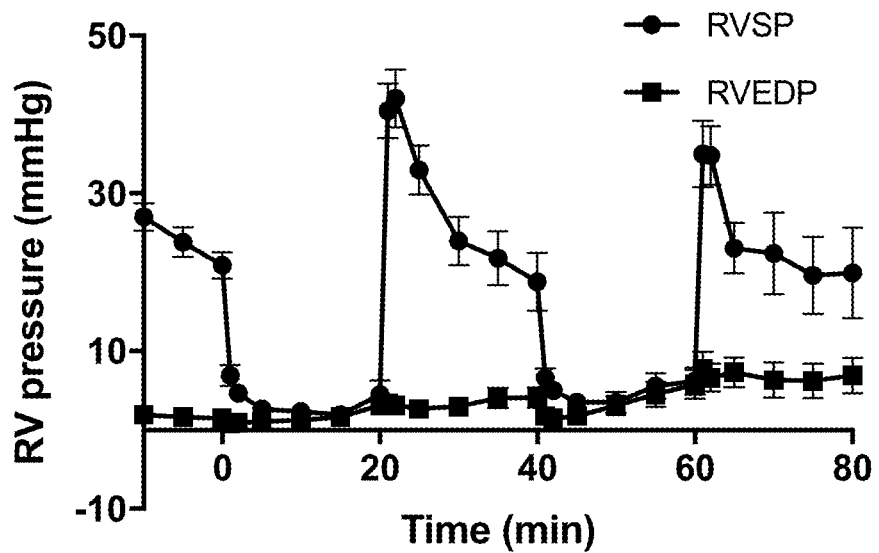
FIG. 8A is a graph of RVSP and RVEDP vs. time (−10 min is when the DMSO was added to the perfusate; 0 min is when a first ischemia was started) from IR experiments in hearts treated with DMSO (control).
Figure 8B:
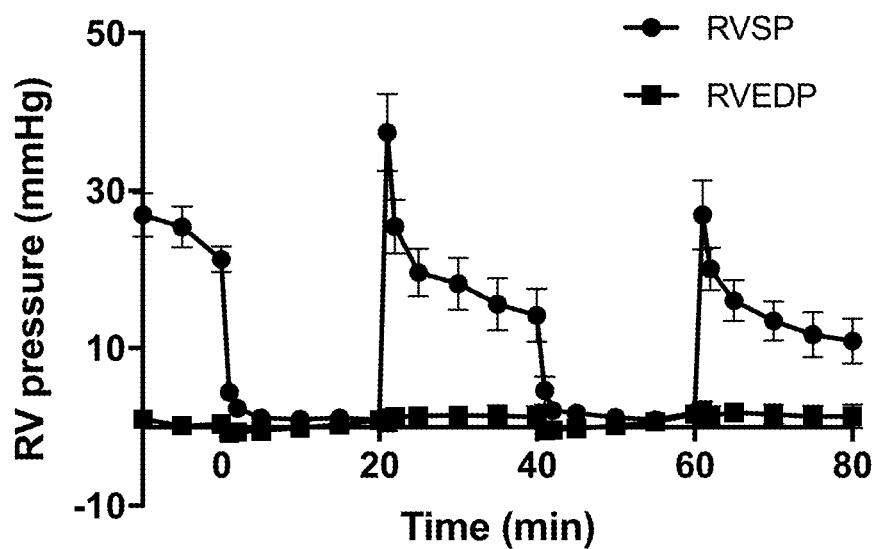
Figure 8C:
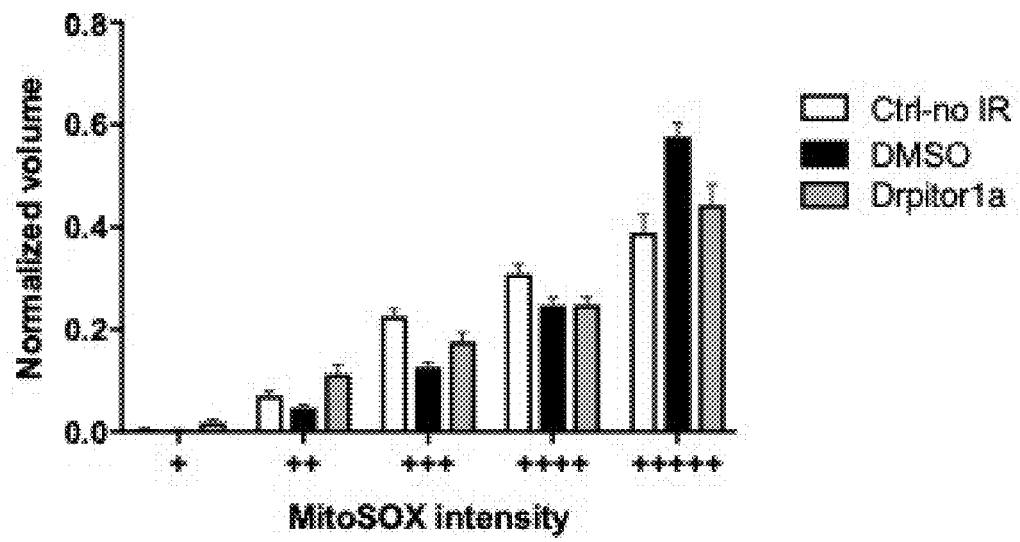
FIG. 8C is a bar graph that shows percentage area having certain levels of MitoSOX vs. intensity level and vs. treatment group.
Figure 8D:
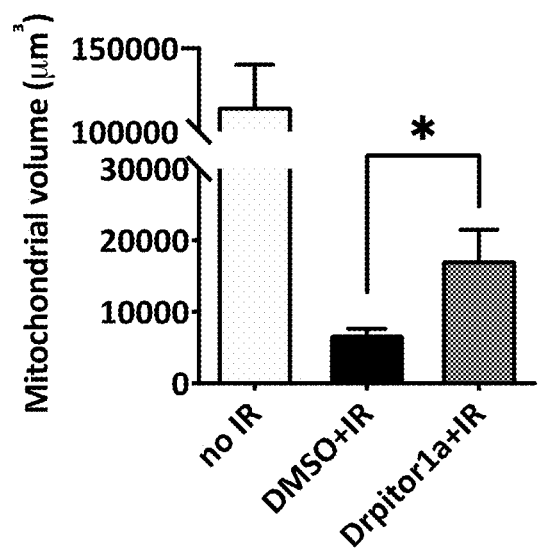
FIG. 8D is a bar graph that shows mitochondrial volume vs. treatment group, wherein mitochondrial volume was significantly increased by Drpitor1a treatment. n=9-19 per group; *P<0.05.

Drp1-mediated mitochondrial fission and the resulting ROS generation and calcium overload play important roles in the pathogenesis of cardiac ischemia-reperfusion (IR) injury. In the right ventricle (RV), IR results in elevated diastolic pressures, compatible with diastolic dysfunction. Previous studies showed that inhibition of Drp1 GTPase activity using a small compound mdivi-1 or inhibition of the interaction between Drp1 and fis1, achieved using a competitive inhibitor peptide of this interaction, P110 protected IR-induced myocardial calcium overload and RV diastolic dysfunction. Here, we investigated the cardioprotective effect of Drpitor1a on RV IR injury, using the Langendorff ex vivo model. Test compound was added to the perfusate prior to IR. A dose of 0.5 µM was used for Drpitor1a. Drpitor1a-treated hearts, did not manifest the increase in right ventricular end-diastolic pressure (RVEDP) that was seen in control hearts after two periods of IR challenge (FIGS. 8A and 8B). After IR, RV myocardium was collected and mitochondrial superoxide was measured. The Drpitor1a-treated RVs had lower MitoSOX intensity during IR compared to control RV, reflecting less production of mitochondrial-derived superoxide (FIG. 8C). Drpitor1a also inhibited Drp1-mediated mitochondrial fission of cardiomyocytes during RV-IR compared to DMSO control, as shown by the increased mean mitochondrial volume (FIG. 8D).

It will be understood by those skilled in the art that this description is made with reference to certain embodiments and that it is possible to make other embodiments employing the principles of the invention which fall within its spirit and scope.

TABLE 1

Identification of candidate compounds from in silico screening and predicted binding affinity and structural formula of compounds of FIG. 1

| Compound Number if assigned | Structure | Predicted Binding Affinity |
|---|---|---|
| 100 | 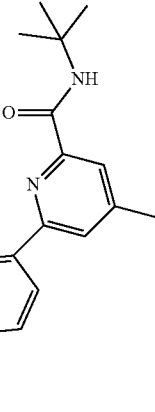 | −11.9 |
| 101 | 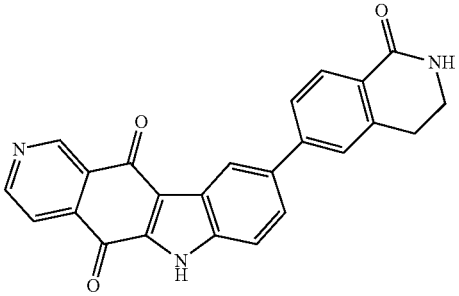 [SMILES: O=C1NCCc2cc(-c3ccc4[nH]c5c(c4c3)C(=O)c3cnccc3C5=O)ccc21] | −11.8 |
| 102 | 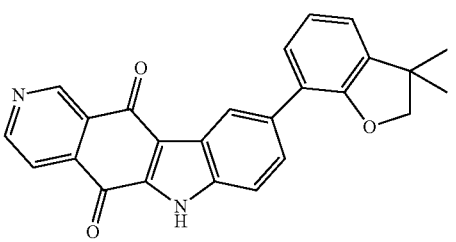 [SMILES: CC1(C)COc2c(-c3ccc4[nH]c5c(c4c3)C(=O)c3cnccc3C5=O)cccc21] | −11.6 |

TABLE 1-continued

Identification of candidate compounds from in silico screening and predicted
binding affinity and structural formula of compounds of FIG. 1

| Compound Number if assigned | Structure | Predicted Binding Affinity |
|---|---|---|
| 103 | 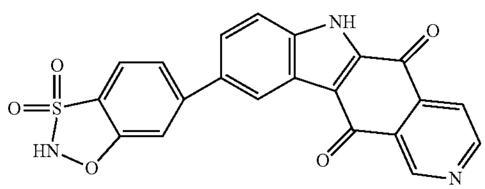 [SMILES: O=C1c2ccncc2C(=O)c2c1[nH]c1ccc(-c3ccc4c(c3)ONS4(=O)=O)cc21] | −11.3 |
| 104 | 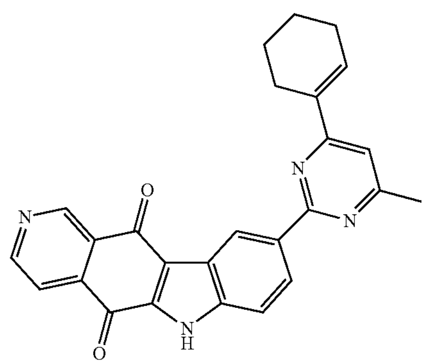 [SMILES: Cc1cc(C2=CCCCC2)nc(-c2ccc3[nH]c4c(c3c2)C(=O)c2cnccc2C4=O)n1] | −11.2 |
| 105 | 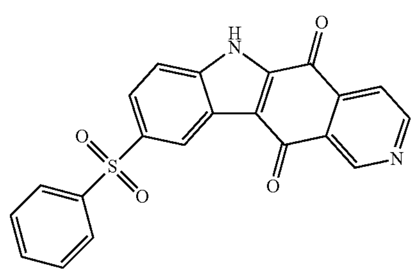 [SMILES: O=C1c2ccncc2C(=O)c2c1[nH]c1ccc(S(=O)(=O)c3ccccc3)cc21] | −11 |
| 106 | 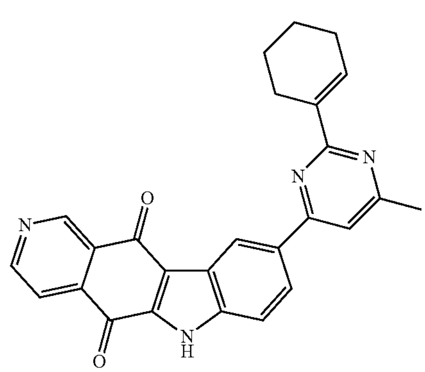 [SMILES: Cc1cc(-c2ccc3[nH]c4c(c3c2)C(=O)c2cnccc2C4=O)nc(C2=CCCCC2)n1] | −11 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 107 | 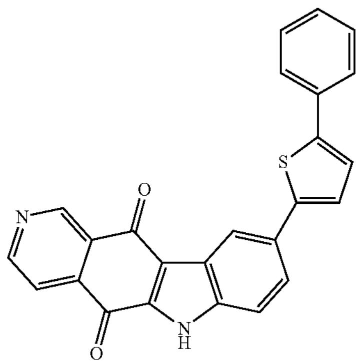 [SMILES: O=C1c2ccncc2C(=O)c2c1[nH]c1ccc(-c3ccc(-c4ccccc4)s3)cc21] | −10.9 |
| 108 | 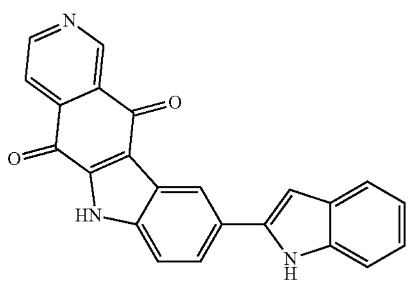 [SMILES: O=C1c2ccncc2C(=O)c2c1[nH]c1ccc(-c3cc4ccccc4[nH]3)cc21] | −10.9 |
| 109 | 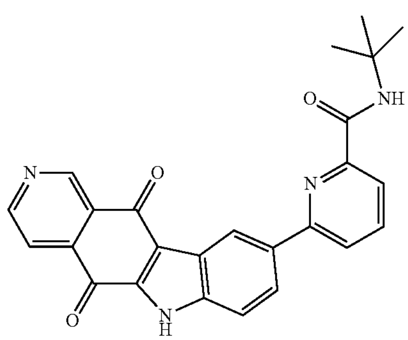 [SMILES: CC(C)(C)NC(=O)c1cccc(-c2ccc3[nH]c4c(c3c2)C(=O)c2cnccc2C4=O)n1] | −10.8 |
| 110 | 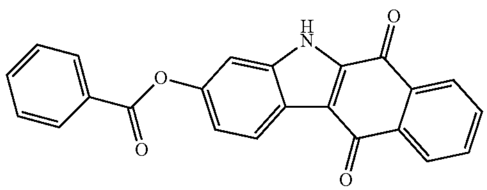 [SMILES: O=C(Oc1ccc2c3c([nH]c2c1)C(=O)c1ccccc1C3=O)c1ccccc1] | −10.8 |
| 111 | 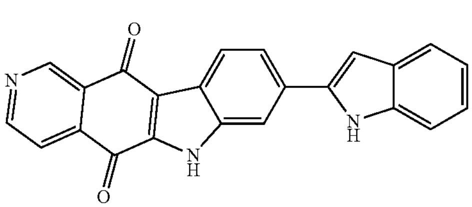 [SMILES: O=C1c2ccncc2C(=O)c2c1[nH]c1cc(-c3cc4ccccc4[nH]3)ccc21] | −10.8 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 112 | 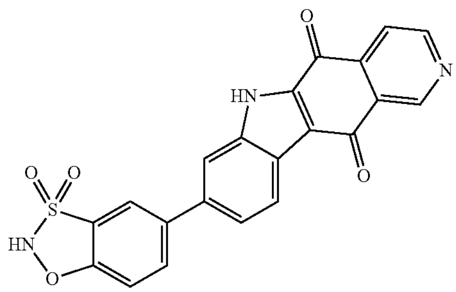 [SMILES: O=C1c2ccncc2C(=O)c2c1[nH]c1cc(-c3ccc4c(c3)S(=O)(=O)NO4)ccc21] | −10.8 |
| 113 | 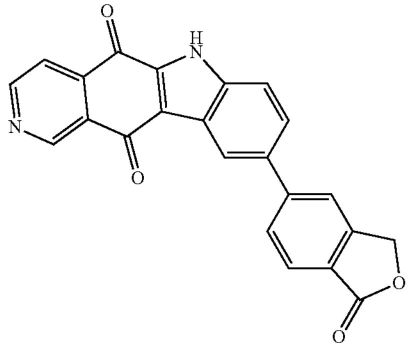 [SMILES: O=C1OCc2cc(-c3ccc4[nH]c5c(c4c3)C(=O)c3cnccc3C5=O)ccc21] | −10.8 |
| 114 | 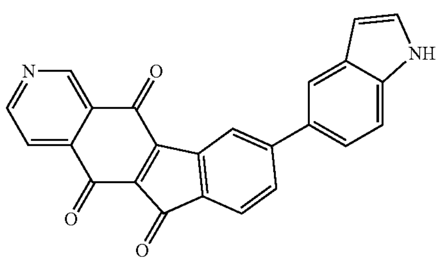 [SMILES: O=c1c2c(=O)c3ccc(-c4ccc5[nH]ccc5c4)cc3c=2c(=O)c2cnccc12] | −10.8 |
| 115 | 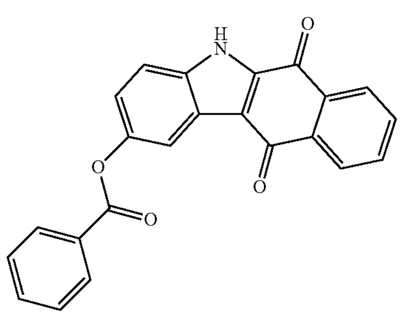 [SMILES: O=C(Oc1ccc2[nH]c3c(c2c1)C(=O)c1ccccc1C3=O)c1ccccc1] | −10.7 |
| 116 | 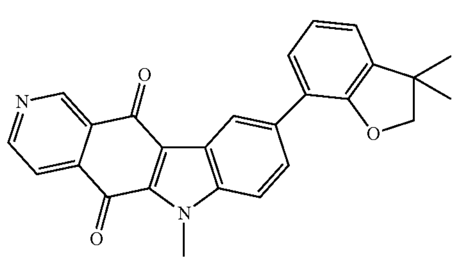 [SMILES: Cn1c2c(c3cc(-c4cccc5c4OCC5(C)C)ccc31)C(=O)c1cnccc1C2=O] | −10.6 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 117 | 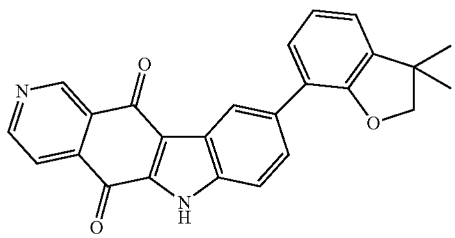 [SMILES: CC1(C)COc2c(-c3ccc4[nH]c5c(c4c3)C(=O)c3cnccc3C5=O)cccc21] | −10.6 |
| 118 | 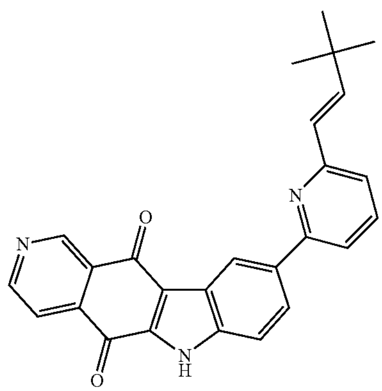 [SMILES: CC(C)(C)/C=C/c1cccc(-c2ccc3[nH]c4c(c3c2)C(=O)c2cnccc2C4=O)n1] | −10.4 |
| 119 | 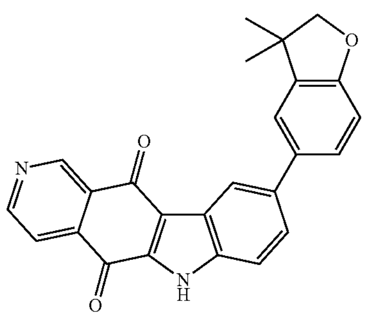 [SMILES: CC1(C)COc2ccc(-c3ccc4[nH]c5c(c4c3)C(=O)c3cnccc3C5=O)cc21] | −10.4 |
| 120 | 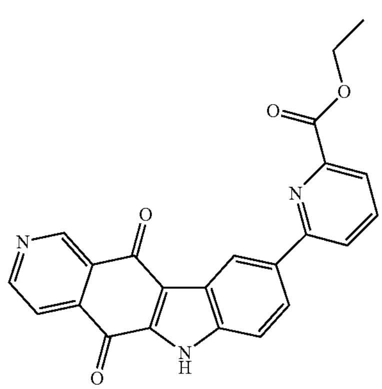 [SMILES: CCOC(=O)c1cccc(-c2ccc3[nH]c4c(c3c2)C(=O)c2cnccc2C4=O)n1] | −10.1 |

TABLE 1-continued

Identification of candidate compounds from in silico screening and predicted
binding affinity and structural formula of compounds of FIG. 1

| Compound Number if assigned | Structure | Predicted Binding Affinity |
|---|---|---|
| 121 | 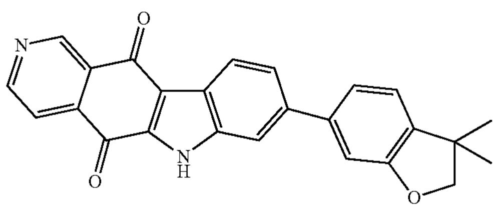 [SMILES: CC1(C)COc2cc(-c3ccc4c5c([nH]c4c3)C(=O)c3ccncc3C5=O)ccc21] | −10.1 |
| 122 | 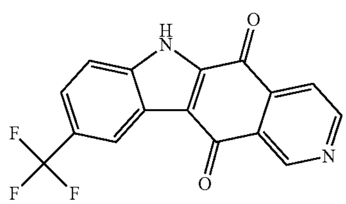 [SMILES: O=C1c2ccncc2C(=O)c2c1[nH]c1ccc(C(F)(F)F)cc21] | −10 |
| 123 | 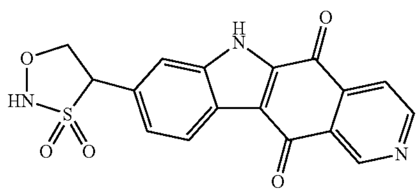 [SMILES: O=C1c2ccncc2C(=O)c2c1[nH]c1cc(C3CONS3(=O)=O)ccc21] | −9.9 |
| 124 | 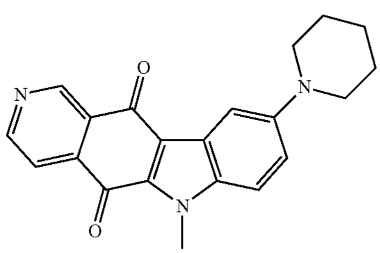 [SMILES: Cn1c2c(c3cc(N4CCCCC4)ccc31)C(=O)c1cnccc1C2=O] | −9.8 |
| 125 | 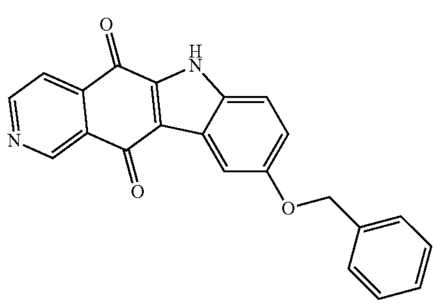 [SMILES: O=C1c2ccncc2C(=O)c2c1[nH]c1ccc(OCc3ccccc3)cc21] | −9.8 |
| 126 | 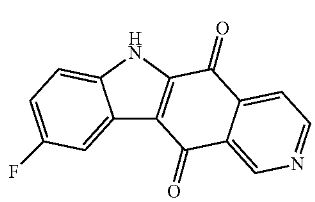 [SMILES: O=C1c2ccncc2C(=O)c2c1[nH]c1ccc(F)cc21] | −9.8 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 127 | 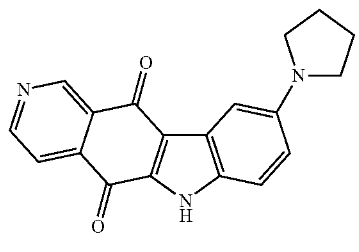 [SMILES: O=C1c2ccncc2C(=O)c2c1[nH]c1ccc(N3CCCC3)cc21] | −9.7 |
| 128 | 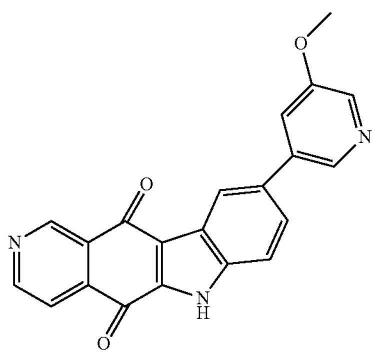 [SMILES: COc1cncc(-c2ccc3[nH]c4c(c3c2)C(=O)c2cnccc2C4=O)c1] | −9.7 |
| 129 | 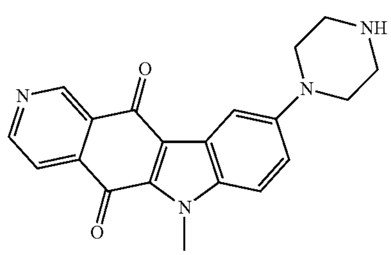 [SMILES: Cn1c2c(c3cc(N4CCNCC4)ccc31)C(=O)c1cnccc1C2=O] | −9.7 |
| 130 | 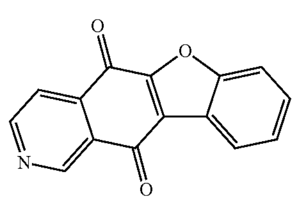 [SMILES: O=C1c2ccncc2C(=O)c2c1oc1ccccc21] | −9.7 |
| 131 | 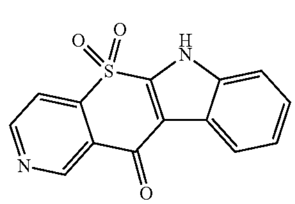 [SMILES: O=C1c2cnccc2S(=O)(=O)c2[nH]c3ccccc3c21] | −9.7 |

TABLE 1-continued

Identification of candidate compounds from in silico screening and predicted
binding affinity and structural formula of compounds of FIG. 1

| Compound Number if assigned | Structure | Predicted Binding Affinity |
|---|---|---|
| 132 | 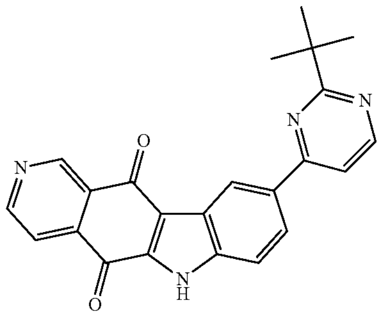 [SMILES: CC(C)(C)c1nccc(-c2ccc3[nH]c4c(c3c2)C(=O)c2cnccc2C4=O)n1] | −9.6 |
| 133 | 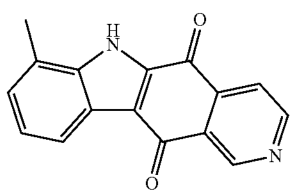 [SMILES: Cc1cccc2c3c([nH]c12)C(=O)c1ccncc1C3=O] | −9.6 |
| 134 | 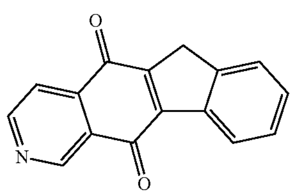 [SMILES: O=C1C2=C(C(=O)c3cnccc31)c1ccccc1C2] | −9.6 |
| 135 | 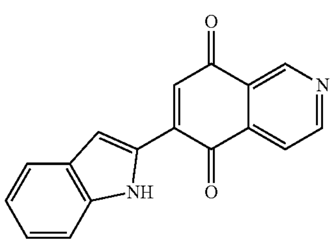 [SMILES: O=C1C=C(c2cc3ccccc3[nH]2)C(=O)c2ccncc21] | −9.5 |
| 136 | 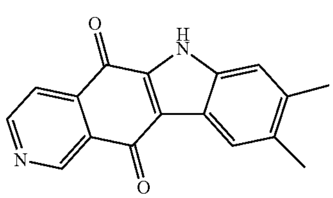 [SMILES: Cc1cc2[nH]c3c(c2cc1C)C(=O)c1cnccc1C3=O] | −9.5 |
| 137 | 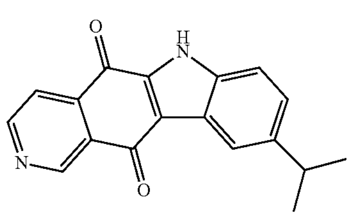 [SMILES: CC(C)c1ccc2[nH]c3c(c2c1)C(=O)c1cnccc1C3=O] | −9.5 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 138 | 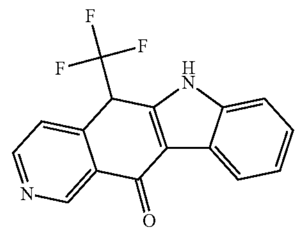 [SMILES: O=C1c2cnccc2C(C(F)(F)F)c2[nH]c3ccccc3c21] | −9.5 |
| 139 | 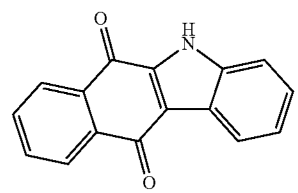 [SMILES: O=C1c2ccccc2C(=O)c2c1[nH]c1ccccc21] | −9.5 |
| 140 | 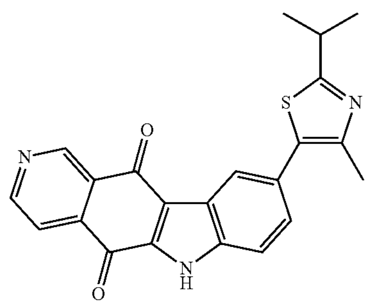 [SMILES: Cc1nc(C(C)C)sc1-c1ccc2[nH]c3c(c2c1)C(=O)c1cnccc1C3=O] | −9.5 |
| 141 | 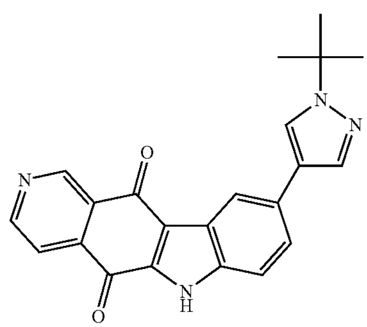 [SMILES: CC(C)(C)n1cc(-c2ccc3[nH]c4c(c3c2)C(=O)c2cnccc2C4=O)cn1] | −9.5 |
| 142 | 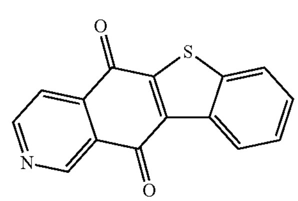 [SMILES: O=C1c2ccncc2C(=O)c2c1sc1ccccc21] | −9.4 |
| 143 | 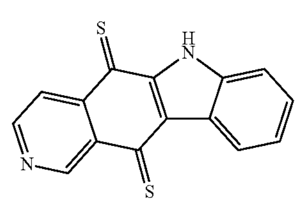 [SMILES: S=C1c2ccncc2C(=S)c2c1[nH]c1ccccc21] | −9.4 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 144 | 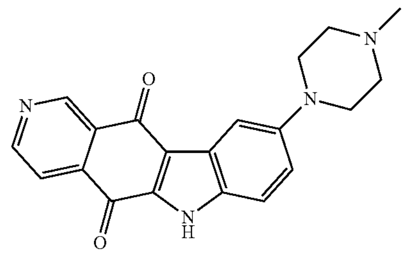 [SMILES: CN1CCN(c2ccc3[nH]c4c(c3c2)C(=O)c2cnccc2C4=O)CC1] | −9.3 |
| 145 | 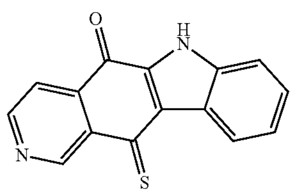 | −9.3 |
| 146 | 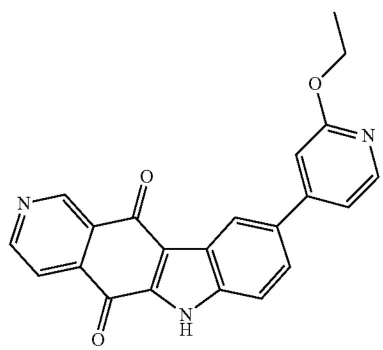 [SMILES: CCOc1cc(-c2ccc3[nH]c4c(c3c2)C(=O)c2cnccc2C4=O)ccn1] | −9.2 |
| 147 | 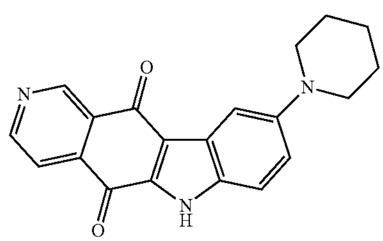 [SMILES: O=C1c2ccncc2C(=O)c2c1[nH]c1ccc(N3CCCCC3)cc21] | −9.2 |
| 148 | 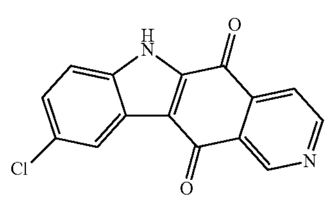 [SMILES: O=C1c2ccncc2C(=O)c2c1[nH]c1ccc(Cl)cc21] | −9.2 |
| 149 | 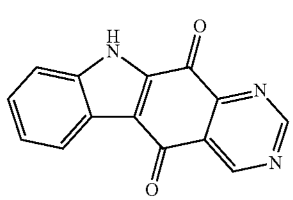 [SMILES: O=C1c2ncncc2C(=O)c2c1[nH]c1ccccc21] | −9.2 |

TABLE 1-continued

Identification of candidate compounds from in silico screening and predicted
binding affinity and structural formula of compounds of FIG. 1

| Compound Number if assigned | Structure | Predicted Binding Affinity |
|---|---|---|
| 150 | 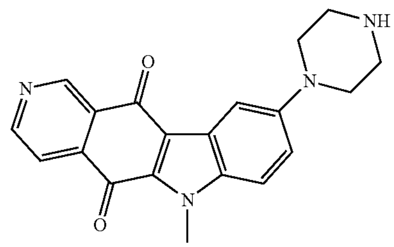 [SMILES: Cn1c2c(c3cc(N4CCNCC4)ccc31)C(=O)c1cnccc1C2=O] | −9 |
| 151 | 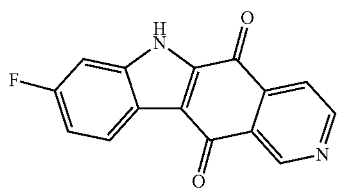 [SMILES: O=C1c2ccncc2C(=O)c2c1[nH]c1cc(F)ccc21] | −9 |
| 152 | 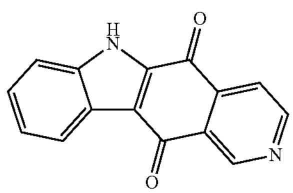 [SMILES: O=C1c2ccncc2C(=O)c2c1[nH]c1ccccc21] | −9 |
| 153 | 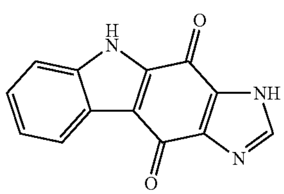 [SMILES: O=C1c2[nH]cnc2C(=O)c2c1[nH]c1ccccc21] | −8.9 |
| 154 | 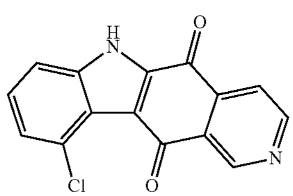 [SMILES: O=C1c2ccncc2C(=O)c2c1[nH]c1cccc(Cl)c21] | −8.9 |
| 155 | 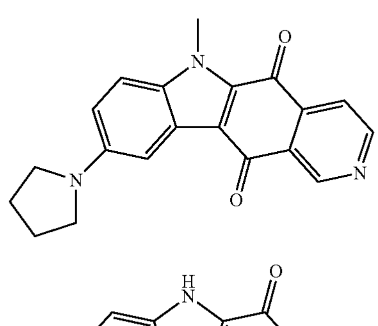 | −8.8 |
| 156 | 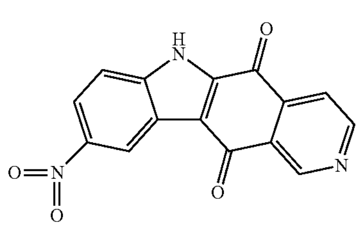 [SMILES: O=C1c2ccncc2C(=O)c2c1[nH]c1ccc([N+](=O)[O-])cc21] | −8.8 |

TABLE 1-continued
Identification of candidate compounds from in silico screening and predicted binding affinity and structural formula of compounds of FIG. 1
| Compound Number if assigned | Structure | Predicted Binding Affinity |
|---|---|---|
| 157 | 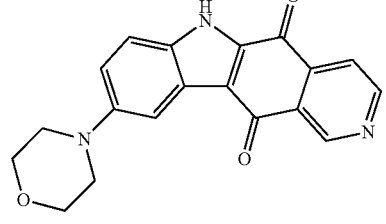 | −8.8 |
| 158 | 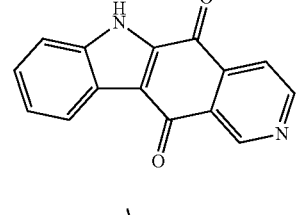 | −8.8 |
| 159 | 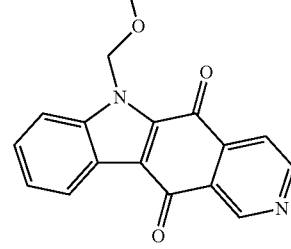 | −8.8 |
| 160 | 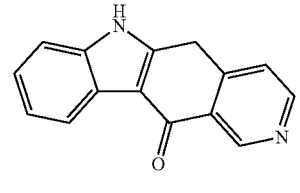 [SMILES: O=C1c2cnccc2Cc2[nH]c3ccccc3c21] | −8.8 |
| 161 | 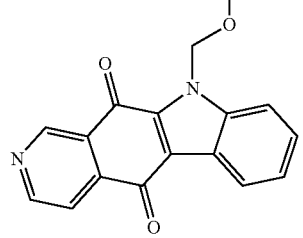 | −8.8 |
| 162 | 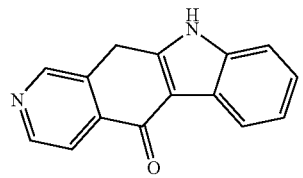 [SMILES: O=C1c2ccncc2Cc2[nH]c3ccccc3c21] | −8.8 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 163 | 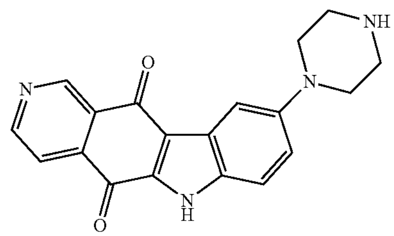 [SMILES: O=C1c2ccncc2C(=O)c2c1[nH]c1ccc(N3CCNCC3)cc21] | −8.7 |
| 164 | 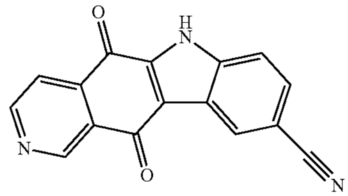 [SMILES: N#Cc1ccc2[nH]c3c(c2c1)C(=O)c1cnccc1C3=O] | −8.7 |
| 165 | 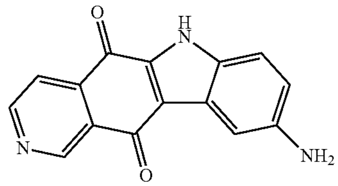 [SMILES: Nc1ccc2[nH]c3c(c2c1)C(=O)c1cnccc1C3=O] | −8.7 |
| 166 | 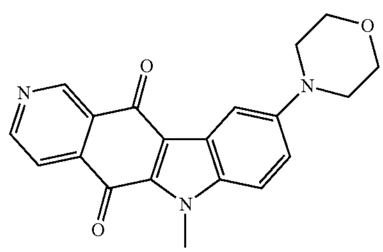 [SMILES: Cn1c2c(c3cc(N4CCOCC4)ccc31)C(=O)c1cnccc1C2=O] | −8.7 |
| 167 | 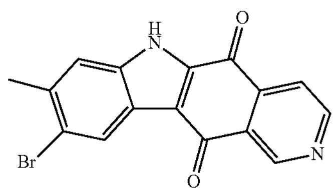 [SMILES: Cc1cc2[nH]c3c(c2cc1Br)C(=O)c1cnccc1C3=O] | −8.7 |
| 168 | 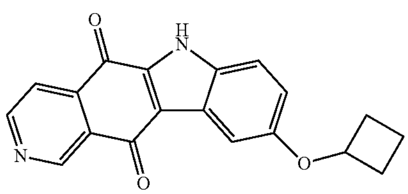 [SMILES: O=C1c2ccncc2C(=O)c2c1[nH]c1ccc(OC3CCC3)cc21] | −8.7 |
| 169 | 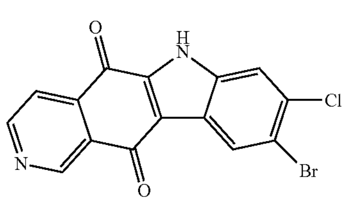 [SMILES: O=C1c2ccncc2C(=O)c2c1[nH]c1cc(Cl)c(Br)cc21] | −8.6 |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 170 | 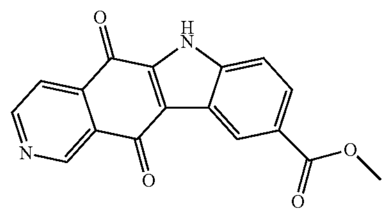 [SMILES: COC(=O)c1ccc2[nH]c3c(c2c1)C(=O)c1cnccc1C3=O] | −8.6 |
| 171 | 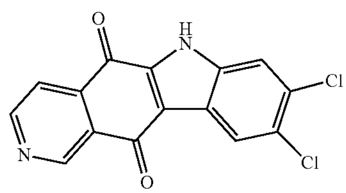 [SMILES: O=C1c2ccncc2C(=O)c2c1[nH]c1cc(Cl)c(Cl)cc21] | −8.5 |
| 172 | 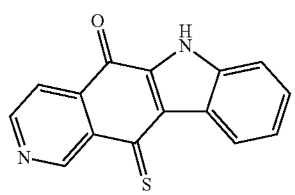 [SMILES: O=C1c2ccncc2C(=S)c2c1[nH]c1ccccc21] | −8.5 |
| 173 | 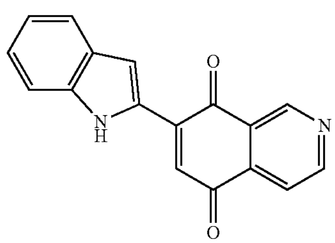 [SMILES: O=C1C=C(c2cc3ccccc3[nH]2)C(=O)c2cnccc21] | −8.4 |
| 174 | 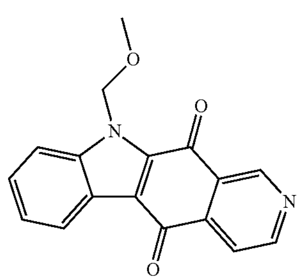 [SMILES: COCn1c2c(c3ccccc31)C(=O)c1ccncc1C2=O] | −8.3 |
| 175 | 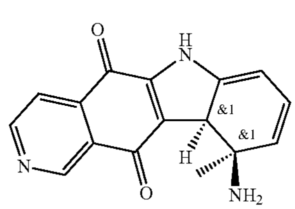 [SMILES: C[C@@]1(N)C=CC=C2NC3=C(C(=O)c4cnccc4C3=O)[C@@H]21] | −8.3 |

TABLE 1-continued

Identification of candidate compounds from in silico screening and predicted
binding affinity and structural formula of compounds of FIG. 1

| Compound Number if assigned | Structure | Predicted Binding Affinity |
|---|---|---|
| 176 | 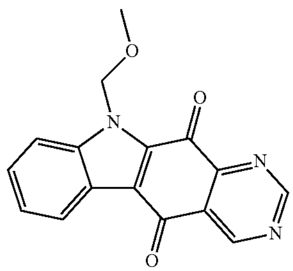 [SMILES: COCn1c2c(c3ccccc31)C(=O)c1cncnc1C2=O] | −8.2 |
| 177 | 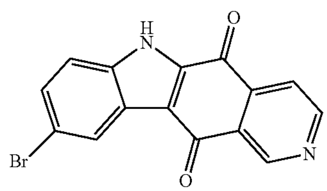 | −8 |
| 178 | 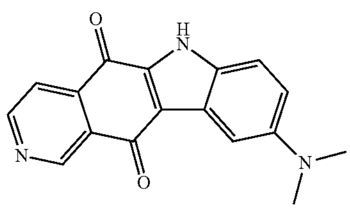 [SMILES: CN(C)c1ccc2[nH]c3c(c2c1)C(=O)c1cnccc1C3=O] | −8 |
| 179 | 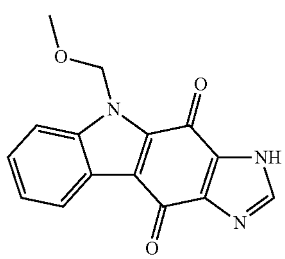 [SMILES: COCn1c2c(c3ccccc31)C(=O)c1nc[nH]c1C2=O] | −7.9 |
| 180 | 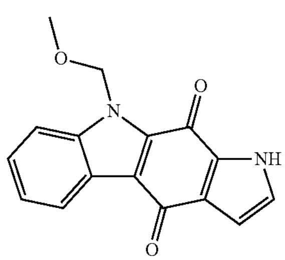 [SMILES: COCn1c2c(c3ccccc31)C(=O)c1cc[nH]c1C2=O] | −7.8 |
| 181 | 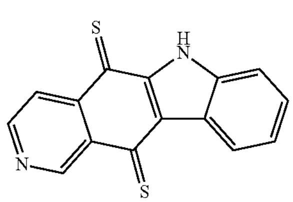 | −7.5 |

TABLE 1-continued
Identification of candidate compounds from in silico screening and predicted binding affinity and structural formula of compounds of FIG. 1
| Compound Number if assigned | Structure | Predicted Binding Affinity |
|---|---|---|
| 1 | 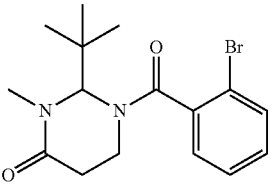 [SMILES: CN1C(=O)CCN(C(=O)c2ccccc2Br)C1C(C)(C)C] | |
| 2 | 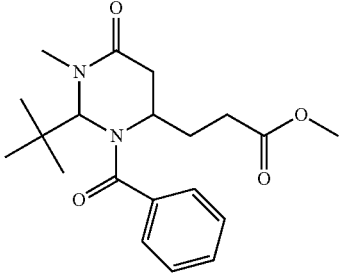 [SMILES: COC(=O)CCC1CC(=O)N(C)C(C(C)(C)C)N1C(=O)c1ccccc1] | |
| 3 | 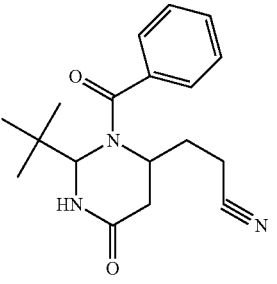 [SMILES: CC(C)(C)C1NC(=O)CC(CCC#N)N1C(=O)c1ccccc1] | |
| 4 | 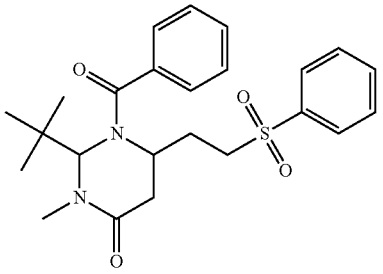 [SMILES: CN1C(=O)CC(CCS(=O)(=O)c2ccccc2)N(C(=O)c2ccccc2)C1C(C)(C)C] | |
| 5 | 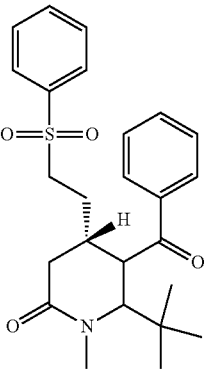 | |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 6 | 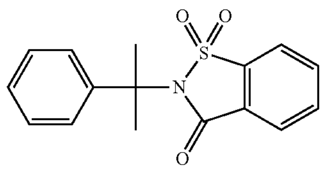 [SMILES: CC(C)(c1ccccc1)N1C(=O)c2ccccc2S1(=O)=O] | |
| 7 | 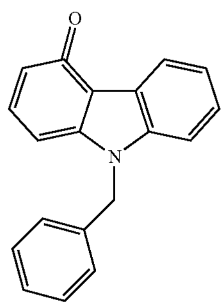 | |
| 8 | 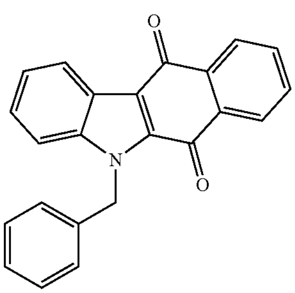 [SMILES: O=C1c2ccccc2C(=O)c2c1c1ccccc1n2Cc1ccccc1] | |
| 9 | 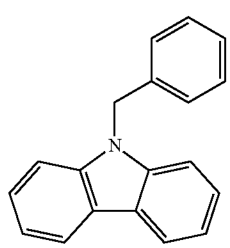 [SMILES: c1ccc(Cn2c3ccccc3c3ccccc32)cc1] | |
| 10 | 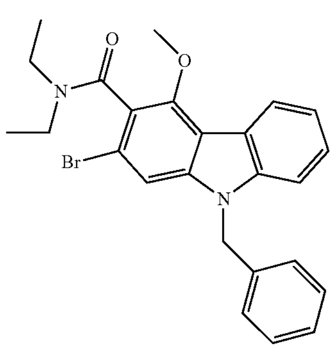 [SMILES: CCN(CC)C(=O)c1c(Br)cc2c(c1OC)c1ccccc1n2Cc1ccccc1] | |

TABLE 1-continued

Identification of candidate compounds from in silico screening and predicted binding affinity and structural formula of compounds of FIG. 1

| Compound Number if assigned | Structure | Predicted Binding Affinity |
|---|---|---|
| 11 | 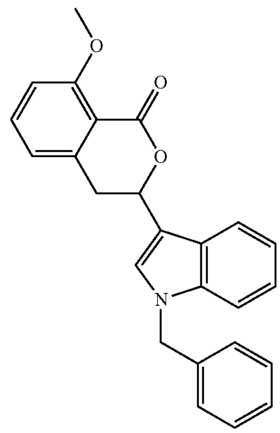 [SMILES: COc1cccc2c1C(=O)OC(c1cn(Cc3ccccc3)c3ccccc13)C2] | |
| 12 "Drpitor1" | 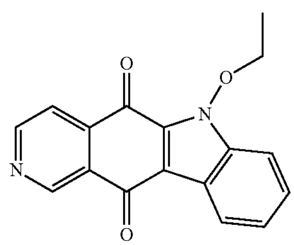 [SMILES: CCOn1c2c(c3ccccc31)C(=O)c1cnccc1C2=O] | |
| 13 | 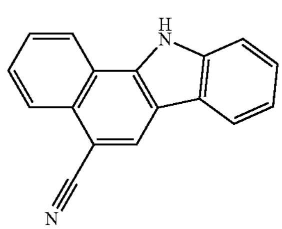 [SMILES: N#Cc1cc2c3ccccc3[nH]c2c2ccccc12] | |
| 14 | 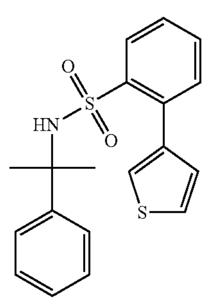 [SMILES: CC(C)(NS(=O)(=O)c1ccccc1-c1ccsc1)c1ccccc1] | |

TABLE 1-continued

Identification of candidate compounds from in silico screening and predicted
binding affinity and structural formula of compounds of FIG. 1

| Compound Number if assigned | Structure | Predicted Binding Affinity |
|---|---|---|
| 15 | 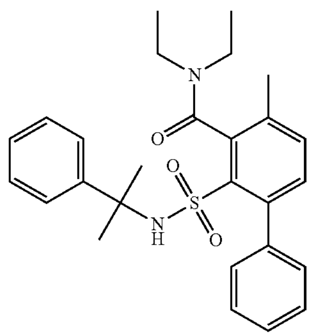 [SMILES: CCN(CC)C(=O)c1c(C)ccc(-c2ccccc2)c1S(=O)(=O)NC(C)(C)c1ccccc1] | |
| 16 | 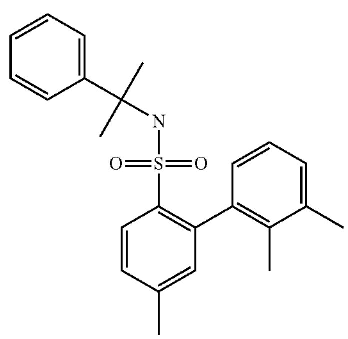 [SMILES: Cc1ccc(S(=O)(=O)NC(C)(C)c2ccccc2)c(-c2cccc(C)c2C)c1] | |
| 17 | 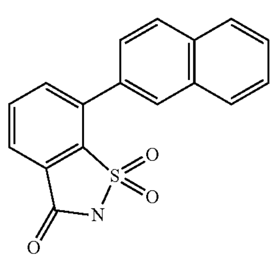 [SMILES: O=C1NS(=O)(=O)c2c1cccc2-c1ccc2ccccc2c1] | |

TABLE 2

Molinspiration bioactivity score showing compound
Drpitor1 and Drpitor1a are predicted to be
kinase inhibitors and enzyme inhibitors

| Molinspiration bioactivity score | Drpitor1 | Drpitor1a |
|---|---|---|
| GPCR ligand | −0.01 | −0.01 |
| Ion channel modulator | 0.03 | 0.21 |
| Kinase inhibitor | 0.49 | 0.50 |
| Nuclear receptor ligand | −0.19 | −0.25 |
| Protease inhibitor | −0.13 | −0.19 |
| Enzyme inhibitor | 0.52 | 0.57 |

TABLE 3

Predicted binding energies of compound Drpitor1, Drpitor1a and mdivi-1 to Drp1 and Dynamin 1 and structural formulae of Dyngo4a

| Compound | Structure | Drp1 (4H1V) | Dynamin 1 (5D3Q) |
|---|---|---|---|
| Drpitor1 | 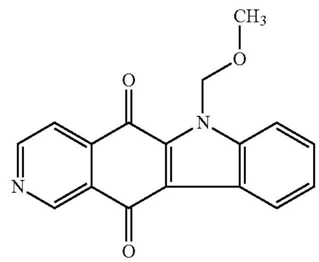 [SMILES: COCn1c2c(c3ccccc31)C(=O)c1cnccc1C2=O] | −8.4 | −7.8 |
| Drpitor1a | 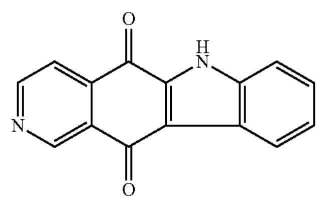 [SMILES: O=C1c2ccncc2C(=O)c2c1[nH]c1ccccc21] | −9.1 | −8.3 |
| mdivi-1 | 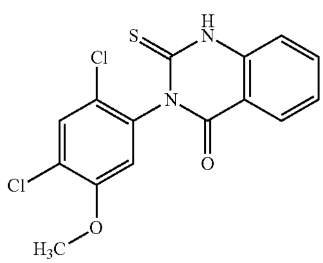 [SMILES: COc1cc(-n2c(=S)[nH]c3ccccc3c2=O)c(Cl)cc1Cl] | −7.2 | −8.4 |
| Dyngo4a | 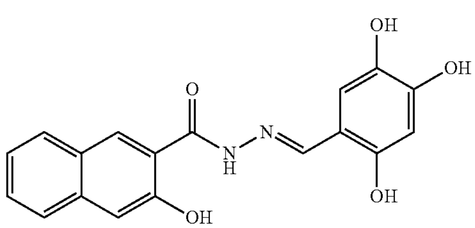 [SMILES: O=C(N/N=C/c1cc(O)c(O)cc1O)c1cc2ccccc2cc1O] | | |

TABLE 4

Inhibition of mitochondrial fragmentation in cancer cell lines by Drpitor1a

| Cell line | MFC (Ctrl) | MFC (Drpitor1a) | Significance (Ctrl vs Drpitor1a) |
|---|---|---|---|
| SK-MES-1 | 0.3186 ± 0.02578 | 0.2291 ± 0.02596 | *$P < 0.05$ |
| SK-LU-1 | 0.4654 ± 0.04816 | 0.3367 ± 0.03623 | *$P < 0.05$ |
| MCF7 | 0.8706 ± 0.1287 | 0.5479 ± 0.05737 | *$P < 0.05$ |
| SW 900 | 0.4836 ± 0.05773 | 0.3345 ± 0.03090 | *$P < 0.05$ |

Ctrl, control; MFC, mitochondrial fragmentation count.
A dose of 0.1-0.5 μM of Drpitor1a was used.

TABLE 5

Inhibition of cell proliferation in cancer cell lines by Drpitors

| Cell line | Cell proliferation (Ctrl) | Cell proliferation (mdivi-1) | Cell proliferation (Drpitor1) | Cell proliferation (Drpitor1a) | P value (Ctrl vs Drpitor1a) |
|---|---|---|---|---|---|
| A549 | 82.95 ± 0.8354 | 32.43 ± 1.481 | 21.83 ± 1.906 | 46 ± 0.8505 | ****$P < 0.0001$ |
| SK-MES-1 | 45.23 ± 0.8373 | 24.97 ± 3.38 | N/A | 5.523 ± 0.3613 | ****$P < 0.0001$ |
| SK-LU-1 | 71.2 ± 1.015 | 29.5 ± 1.652 | N/A | 5.04 ± 0.5525 | ****$P < 0.0001$ |
| SW 900 | 82.6 ± 0.5568 | 50.1 ± 0.7211 | N/A | 28.37 ± 0.3712 | ****$P < 0.0001$ |
| MCF7 | 68.23 ± 1.037 | 8.217 ± 1.256 | N/A | 3.437 ± 0.2325 | ****$P < 0.0001$ |

A dosage of 0.5 μM of Drpitor1a was used.

TABLE 6

Inhibition of cell survival in cancer cell lines by Drpitor1a

| Cell line | Colony number (Ctrl) | Colony number (mdivi-1) | Colony number (Drpitor1a) | P value (Ctrl vs Drpitor1a) |
|---|---|---|---|---|
| A549 | 30.83 ± 4.799 | 0.5 ± 0.3416 | 1.5 ± 0.2236 | ****$P < 0.0001$ |
| SK-MES-1 | 10.17 ± 0.8333 | 5.5 ± 0.5627 | 0 ± 0 | ****$P < 0.0001$ |
| SK-LU-1 | 4.333 ± 0.8433 | 2.5 ± 0.4282 | 0.6667 ± 0.3333 | ***$P < 0.001$ |
| MCF7 | 10.17 ± 0.7923 | 7.167 ± 0.7491 | 0 ± 0 | ****$P < 0.0001$ |

A dosage of 0.5 μM of Drpitor1a was used.

TABLE 7

Cell apoptosis in cancer cell lines induced by Drpitors

| Cell line | Apoptosis (Ctrl) | Apoptosis (mdivi-1) | Apoptosis (Drpitor1) | Apoptosis (Drpitor1a) | P value (Ctrl vs Drpitor1a) |
|---|---|---|---|---|---|
| A549 | 8.04 ± 1.466 | 15.3 ± 0.5213 | 14.36 ± 1.619 | 25.06 ± 0.4675 | ****$P < 0.0001$ |
| SK-MES-1 | 1.3 ± 0.04743 | N/A | N/A | 2.464 ± 0.131 | ****$P < 0.0001$ |
| SK-LU-1 | 2.748 ± 0.1877 | N/A | N/A | 3.6 ± 0.2292 | *$P < 0.05$ |
| SW 900 | 2.868 ± 0.0893 | N/A | N/A | 5.686 ± 0.1402 | ****$P < 0.0001$ |

Dosages of 1.0 μM of Drpitor1 and 0.25-0.5 μM of Drpitor1a were used.

TABLE 8

Drpitor1a does not cause liver and kidney toxicity

| Parameter | Ctrl | Drpitor1a | P value |
|---|---|---|---|
| Albumin (g/L) | 40.33 ± 9.387 | 26.75 ± 0.9465 | ns |
| Total bilirubin (μmol/L) | 50.43 ± 44.45 | 2.5 ± 0.324 | ns |
| Cholesterol (mmol/L) | 8.04 ± 2.873 | 4.188 ± 0.3317 | ns |
| BUN (mmol/L) | 8.833 ± 0.2963 | 6.225 ± 1.186 | ns |

BUN, blood urea nitrogen; ns, not significant.
A dose of 10 mg/kg of Drpitor1a was used.

TABLE 9

Drpitor1a inhibits mitochondrial fragmentation of PAH PASMC cell lines

| Cell line | MFC (Ctrl) | MFC (mdivi-1) | MFC (Drpitor1a) | P value (Ctrl vs Drpitor1a) |
|---|---|---|---|---|
| P1 | 0.2041 ± 0.01529 | 0.1394 ± 0.01072 | 0.1339 ± 0.01669 | *P < 0.05 |
| P3 | 0.3364 ± 0.02963 | 0.2667 ± 0.02021 | 0.2061 ± 0.01332 | ***P < 0.001 |
| P7 | 0.3233 ± 0.04189 | 0.2354 ± 0.022 | 0.2095 ± 0.02134 | *P < 0.05 |

PAH, pulmonary arterial hypertension; PASMC, pulmonary artery smooth muscle cells; MFC, mitochondrial fragmentation count.
A dose of 0.1 μM of Drpitor1a was used.

TABLE 10

Drpitor1a inhibits cell proliferation of PAH PASMC cell lines

| Cell line | Cell proliferation (Ctrl) | Cell proliferation (mdivi-1) | Cell proliferation (Drpitor1a) | P value (Ctrl vs Drpitor1a) |
|---|---|---|---|---|
| P1 | 16.27 ± 0.3667 | 7.38 ± 0.1762 | 3.367 ± 0.3335 | ****P < 0.0001 |
| P3 | 0.9 ± 0.05292 | 0.3567 ± 0.04372 | 0.7167 ± 0.05608 | ns |
| P7 | 17.4 ± 0.8185 | 7.78 ± 0.1882 | 9.68 ± 0.563 | ***P < 0.001 | ns, not significant.
A dosage of 1.0 μM of Drpitor1a was used.

TABLE 11

Drpitor1a inhibits cell proliferation of brain tumor cell lines

| Cell line | Cell proliferation (Ctrl) | Cell proliferation (mdivi-1) | Cell proliferation (Drpitor1a) | P value (Ctrl vs Drpitor1a) |
|---|---|---|---|---|
| Daoy cells (Medulloblastoma cells) | 1 ± 0.003803 | 0.8464 ± 0.008105 | 0.7078 ± 0.005519 | ***P < 0.001 |
| U373 (Glioblastoma cells) | 87.2 ± 0.3215 | 65.43 ± 0.06667 | 45.33 ± 0.2728 | ****P < 0.0001 |
| U87 (Glioblastoma cells) | 1 ± 0.003092 | 0.9552 ± 0.01912 | 0.1084 ± 0.001408 | ****P < 0.0001 |

A dosage of 0.15~2.5 μM of Drpitor1a was used.

We claim:

1. A method for reducing or inhibiting mitochondrial fission, wherein the mitochondrial fission is associated with pulmonary arterial hypertension, comprising administering to a subject in need thereof an effective amount of a pharmaceutical composition comprising:

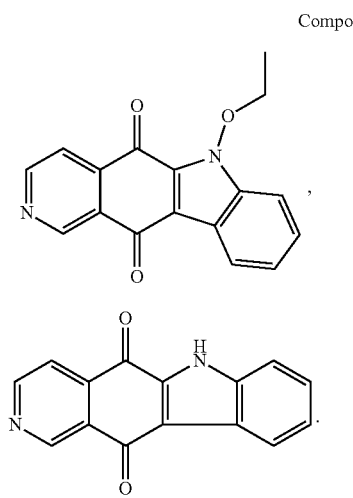

Compound 12 "Drpitor1"

, or

Drpitor1a

2. The method of claim 1, wherein the mitochondrial fission is associated with one or more of cancer, pulmonary arterial hypertension, cardioprotection, stroke, coronary heart disease, a neurodegenerative disease, Parksinonism, Huntington's Chorea, Alzheimer's disease, diabetic cardiomyopathy, fatty liver diseases, non-alcoholic fatty liver diseases, and alcohol-related liver disease.

3. The method of claim 1, wherein the mitochondrial fission is associated with one or more of cancer, pulmonary arterial hypertension, cardioprotection, stroke, coronary heart disease, a neurodegenerative disease, Parksinonism, Huntington's Chorea, Alzheimer's disease, diabetic cardiomyopathy, fatty liver diseases, non-alcoholic fatty liver diseases, and alcohol-related liver disease.

4. The method of claim 2, wherein the cancer is metastatic cancer.

5. The method of claim 4, wherein the metastatic cancer is breast cancer, ovarian cancer, lung cancer, pancreatic cancer, melanoma, colorectal cancer, kidney cancer, cervical cancer, testicular cancer, or liver cancer.

6. The method of claim 1, wherein an effective amount is an amount from 1 to 1000 mg.

7. The method of claim 1, wherein an effective amount is an amount from 5 to 500 mg.

* * * * *